US010448893B2

(12) United States Patent
Armitstead et al.

(10) Patent No.: US 10,448,893 B2
(45) Date of Patent: Oct. 22, 2019

(54) METHOD AND APPARATUS FOR DETECTING RESPIRATORY EFFORT

(75) Inventors: Jeffrey Peter Armitstead, North Sydney (AU); Glenn Richards, Auckland (NZ); Alicia Kristianne Wells, Narrabeen (AU)

(73) Assignee: ResMed Pty Ltd (AU)

( * ) Notice: Subject to any disclaimer, the term of this patent is extended or adjusted under 35 U.S.C. 154(b) by 769 days.

(21) Appl. No.: 13/352,758

(22) Filed: Jan. 18, 2012

(65) Prior Publication Data
US 2012/0190998 A1 Jul. 26, 2012

Related U.S. Application Data

(60) Provisional application No. 61/436,020, filed on Jan. 25, 2011.

(51) Int. Cl.
*A61B 5/113* (2006.01)
*A61B 5/00* (2006.01)
(Continued)

(52) U.S. Cl.
CPC .......... *A61B 5/6814* (2013.01); *A61B 5/0826* (2013.01); *A61B 5/113* (2013.01);
(Continued)

(58) Field of Classification Search
CPC ... A61B 5/6814; A61B 5/0826; A61B 5/4818; A61B 5/113; A61B 5/683
(Continued)

(56) References Cited

U.S. PATENT DOCUMENTS 4,836,219 A * 6/1989 Hobson et al. ............... 600/595
4,860,766 A 8/1989 Sackner
(Continued)

FOREIGN PATENT DOCUMENTS

WO 2010103435 A1 9/2010

OTHER PUBLICATIONS

European Examination Report for Application No. 12152468.0 dated Sep. 9, 2014.
(Continued)

*Primary Examiner* — Etsub D Berhanu
*Assistant Examiner* — Michael Catina
(74) *Attorney, Agent, or Firm* — Botos Churchill IP Law LLP

(57) ABSTRACT

Devices and systems provide methods for detecting respiratory related effort from movements associated with the head or face. In one embodiment, a strain signal is measured by one or more sensors. A processor may analyze the head strain signal to detect respiratory related effort. Detection of effort may serve as a basis for identifying sleep disordered breathing events. For example, the analysis may serve as part of a detector to identify central or obstructive apneas or central or obstructive hypopneas. Sensors may be integrated with headgear to support them at desired locations of the face or head. Strain from head movement may be detected by measuring, for example, tension of the headgear or force applied against the headgear. The headgear may serve as an independent support for the sensors or as a component of a respiratory treatment apparatus, such as a mask or cannula.

62 Claims, 14 Drawing Sheets

(51) Int. Cl.
 A61M 16/00 (2006.01)
 A61M 16/06 (2006.01)
 A61B 5/08 (2006.01)

(52) U.S. Cl.
 CPC .......... *A61B 5/4818* (2013.01); *A61B 5/6831* (2013.01); *A61M 16/0051* (2013.01); *A61M 16/06* (2013.01); *A61M 16/0633* (2014.02); *A61M 16/0683* (2013.01); *A61M 16/0069* (2014.02); *A61M 2016/0027* (2013.01); *A61M 2016/0039* (2013.01); *A61M 2205/332* (2013.01); *A61M 2205/3553* (2013.01); *A61M 2205/3569* (2013.01); *A61M 2205/3584* (2013.01); *A61M 2205/3592* (2013.01); *A61M 2205/502* (2013.01); *A61M 2205/52* (2013.01); *A61M 2205/583* (2013.01)

(58) Field of Classification Search
 USPC .................................................. 600/529, 534
 See application file for complete search history.

(56) References Cited

U.S. PATENT DOCUMENTS

| | | |
|---|---|---|
| 5,199,424 A | 4/1993 | Sullivan et al. |
| 6,675,797 B1 | 1/2004 | Berthon-Jones |
| 6,840,907 B1 | 1/2005 | Brydon |
| 7,730,886 B2 | 6/2010 | Berthon-Jones |
| 2002/0161308 A1 | 10/2002 | Matsumura et al. |
| 2005/0027207 A1* | 2/2005 | Westbrook et al. .......... 600/529 |
| 2005/0074741 A1 | 4/2005 | Lee et al. |
| 2007/0073171 A1* | 3/2007 | Cho et al. .................... 600/486 |
| 2007/0208269 A1* | 9/2007 | Mumford et al. ............ 600/546 |
| 2007/0273366 A1 | 11/2007 | Ansay et al. |
| 2008/0083412 A1* | 4/2008 | Henry et al. ............. 128/207.11 |
| 2010/0147304 A1 | 6/2010 | Burton |
| 2010/0240982 A1 | 9/2010 | Westbrook et al. |
| 2012/0089042 A1* | 4/2012 | Bussa .................... A61B 5/113 600/534 |

OTHER PUBLICATIONS

Somnolter-Jawsens, Devices that detect sleep respiratory disturbances based on an analysis of mandibular movement during sleep, pp. 1-10, Nomics 2007.

European Search Report EP12152468 dated May 18, 2012.

\* cited by examiner

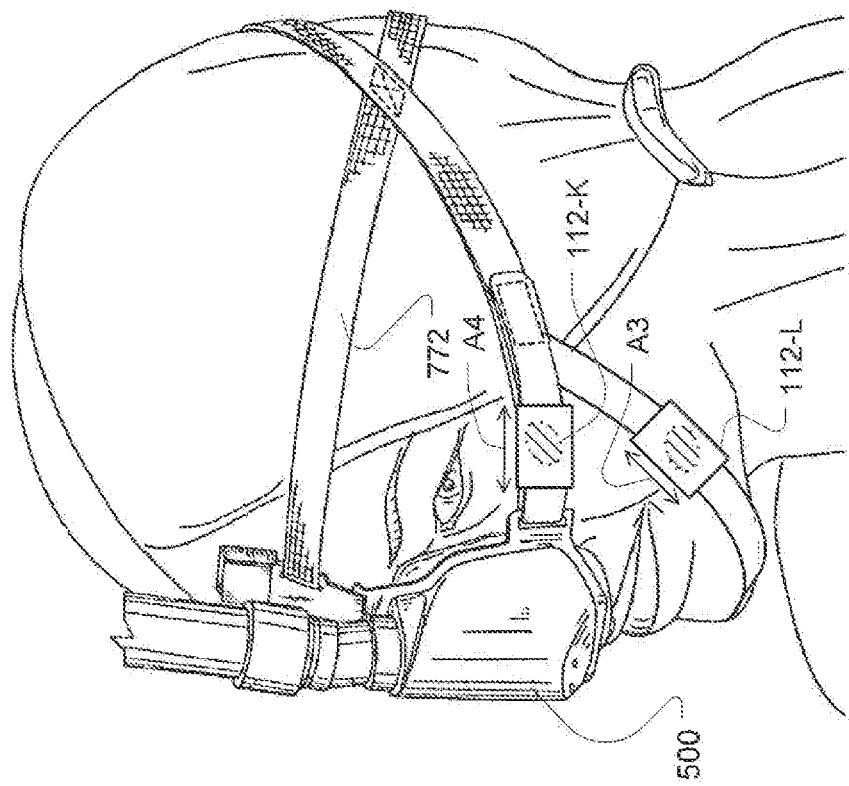
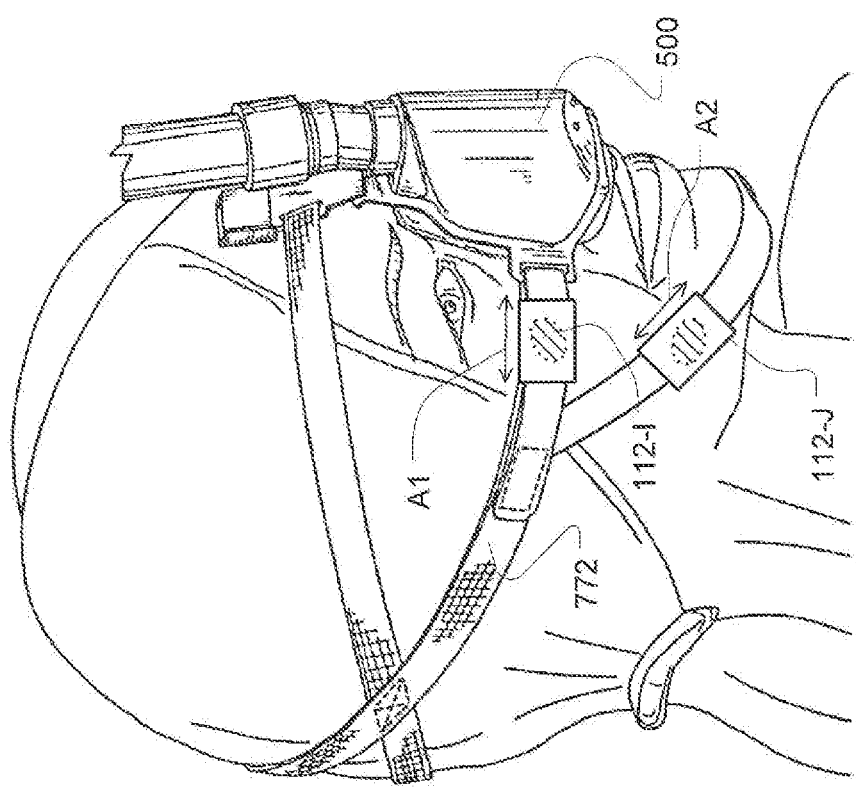

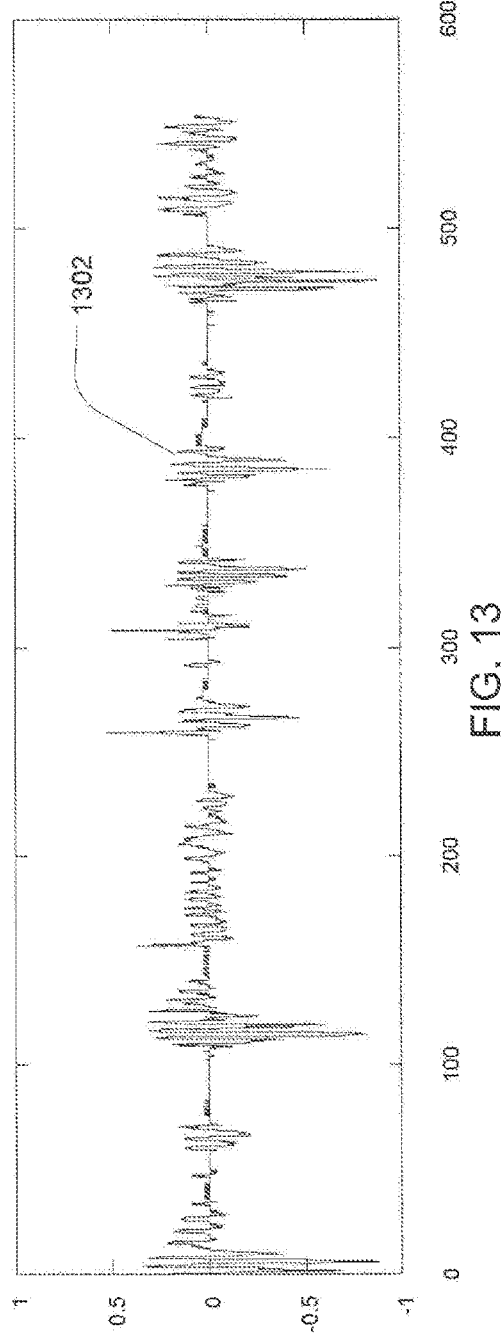
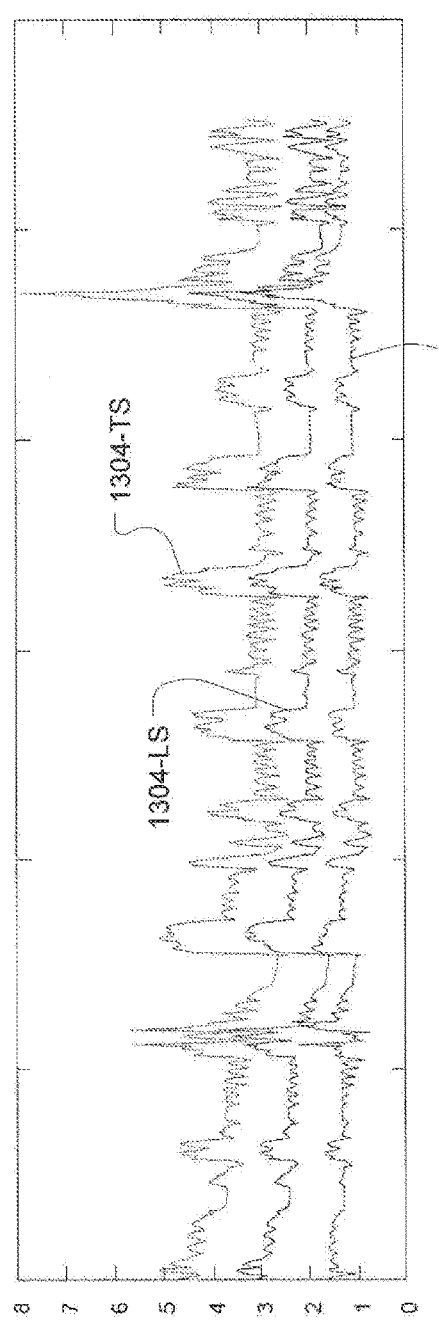

METHOD AND APPARATUS FOR DETECTING RESPIRATORY EFFORT

CROSS REFERENCE TO RELATED APPLICATIONS

This application claims the benefit of the filing date of U.S. Provisional Patent Application No. 61/436,020 filed Jan. 25, 2011, the disclosure of which is hereby incorporated herein by reference.

FIELD OF THE TECHNOLOGY

The present technology relates to methods and apparatus for detecting conditions that relate to respiratory effort or sleep disordered breathing. More particularly, some embodiments of the technology relate to detecting breathing related effort or non-effort from movement associated with the head or face.

BACKGROUND OF THE TECHNOLOGY

As described by Sullivan & Lynch in U.S. Pat. No. 5,199,424, issued on Apr. 6, 1993, the application of continuous positive airway pressure (CPAP) has been used as a means of treating the occurrence of obstructive sleep apnea. The patient is connected to a positive pressure air supply by means of a nose mask or nasal prongs. The air supply breathed by the patient is provided at a pressure that is slightly greater than atmospheric pressure. It has been found that the application of continuous positive airway pressure provides what can be described as a "pneumatic splint", supporting and stabilizing the upper airway and thus eliminating the occurrence of upper airway occlusions. Such a treatment pressure can be effective in eliminating both snoring and obstructive sleep apnea and in many cases, is effective in treating central and mixed apnea.

Detecting apneas and more particularly the type of apnea that a patient is experiencing may be important, as certain types of apneas need to be treated differently.

As described by Berthon-Jones in U.S. Pat. No. 6,675,797, issued on 13 Jan. 2004, central and obstructive apneas can be detected (and distinguished) using a forced oscillation technique. Airway patency is determined by applying an oscillatory pressure waveform and then determining if a component of the air flow indicates that a central or obstructive apnea is occurring. For example, the component may be the amplitude of the air flow signal, and when comparing the patient's amplitude, or its derivative, to a threshold value, this will indicate if a central or obstructive apnea is occurring.

As described by Berthon-Jones in U.S. Pat. No. 7,730,886, issued on 8 Jun. 2010, central apneas can be distinguished from obstructive apneas by analyzing the air flow signal and identifying if there is a cardiogenic component of the air flow signal. For example, if no cardiogenic component of the air flow signal can be detected, the patient will received pressurized breathable gas to treat an obstructive apnea.

Despite the availability of such methods for detecting and distinguishing obstructive and central apnea, some sleep disorder breathing events may still go undetected and thus untreated with the use of some devices. Thus, it will be appreciated that there may be a need for improved techniques and devices for addressing the conditions of sleep disordered breathing.

SUMMARY OF THE TECHNOLOGY

Aspects of some embodiments of the present technology may involve detection of respiratory effort.

Further aspects of some embodiments of the present technology may involve detection of head or facial respiratory effort.

Still further aspects of some embodiments of the present technology may involve detection of respiratory effort from measurements of strain sensors, such as sensors incorporated in headgear for supporting a patient interface.

Some embodiments may also involve the detection of sleep disordered breathing events based on the measured strain signals or the detected respiratory effort.

Still further embodiments may implement the detection and measurement methodologies with monitoring devices, and optionally may also be incorporated into respiratory treatment apparatus, such as a ventilator or positive airway pressure treatment apparatus.

Some embodiments of the technology may involve a method for detecting respiratory related effort. Such a method may include measuring a head strain signal with a sensor and analyzing the head strain signal with a processor to detect respiratory related effort. Optionally, the analyzing may involve a comparison of the head strain signal and a threshold. The threshold may be derived from a prior head strain signal measured with the sensor.

The method may further involve identifying, with the processor, a type of a detected apnea based on the comparison. Optionally, the type of detected apnea may be identified as one of a central apnea and an obstructive apnea. For example, the type of detected apnea may be identified as a central apnea when the analysis detects an absence of facial respiratory effort. Still further, the type of detected apnea may be identified as an obstructive apnea when the analysis detects a presence of facial or head respiratory effort.

The method may further involve identifying, with the processor, a type of a detected hypopnea based on the comparison. For example, the type of detected hypopnea may be identified as a central hypopnea when the analysis detects an absence of facial respiratory effort. Still further, the type of detected hypopnea may be identified as an obstructive hypopnea when the analysis detects a presence of facial respiratory effort.

Optionally, the method may also involve identifying, with the processor, a respiratory related arousal event based on the comparison. In some cases, the method may also involve the controlling of a change to a respiratory treatment variable, such as pressure, flow or ventilation, based on the analyzing of the head strain signal. Optionally, the controlling of the change to the respiratory treatment variable may be further based on an analysis of data derived from an additional sensor, such as a flow sensor.

Some embodiments of the present technology may also involve a device for detecting facial respiratory related effort. The device may include one or more sensors configured to generate a head strain signal. It may also include a processor, coupled with the one or more sensors. This processor may be configured to control detection of respiratory related effort by analysis of the head strain signal. For example, the analysis may involve a comparison of the head strain signal and a threshold. Optionally, the threshold may be derived from a prior head strain signal measured with the sensor.

In some such embodiments, the processor of the device may be configured to identify a type of a detected apnea based on the comparison. For example, the type of detected apnea may be identified as one of a central apnea or an obstructive apnea. Optionally, the type of detected apnea may be identified as a central apnea when the analysis detects an absence of facial respiratory effort or the type of detected apnea may be identified as an obstructive apnea when the analysis detects a presence of facial respiratory effort.

By way of further example, the processor may be configured to identify a type of a detected hypopnea based on the comparison. The type of detected hypopnea may be identified as a central hypopnea when the analysis detects an absence of facial respiratory effort or the type of detected hypopnea may be identified as an obstructive hypopnea when the analysis detects a presence of facial respiratory effort.

In embodiments of the device, the processor may also be configured to identify a respiratory related arousal event based on the comparison. The processor may also be configured to control a change to a respiratory treatment variable, such as pressure, flow or ventilation setting, based on the analysis of the head strain signal. Moreover, the processor may also be configured to analyze data derived from an additional sensor, such that the control of the change to the respiratory treatment variable setting is further based on the analysis by the processor of the data derived from the additional sensor, which may, for example, be a flow sensor.

Additional embodiments of the present technology may be implemented as a respiratory treatment apparatus. The respiratory treatment apparatus may include a patient interface and headgear. The patient interface usually includes a patient mask and may also include one or more sensors configured to generate a head strain signal. The apparatus may further include a flow generator adapted to be coupled to the patient interface. The flow generator may be configured to generate a flow of a breathable gas through the patient interface. The apparatus may also include a processor, coupled with the flow generator, which may be adapted to couple with the one or more sensors. The processor may also be configured to control the flow generator and to control a detection of respiratory related effort by analysis of the head strain signal.

In some embodiments of the apparatus, the analysis may involve a comparison of the head strain signal and a threshold. Optionally, the threshold may be derived from a prior head strain signal measured with the sensor.

The processor of apparatus may also be configured to identify a type of a detected apnea based on the comparison. For example, the type of detected apnea may be identified as one of a central apnea and an obstructive apnea. Still further, the type of detected apnea may be identified as a central apnea when the analysis detects an absence of facial respiratory effort. Optionally, the type of detected apnea may be identified as an obstructive apnea when the analysis detects a presence of facial respiratory effort.

The processor of apparatus may also be configured to identify a type of a detected hypopnea based on the comparison. For example, the type of detected hypopnea may be identified as a central hypopnea when the analysis detects an absence of facial respiratory effort. Moreover, the type of detected hypopnea may be identified as an obstructive hypopnea when the analysis detects a presence of facial respiratory effort. The processor of the apparatus may also be configured to identify a respiratory related arousal event based on the comparison.

In some cases, the processor of the respiratory treatment apparatus may be further configured to control a change to a respiratory treatment variable, such as pressure, flow or ventilation setting of the flow generator of the apparatus based on the analysis of the head strain signal. The processor of the respiratory treatment apparatus may also be configured to analyze data derived from an additional sensor, such that the control of the change to the respiratory treatment variable setting may be further based on the analysis by the processor of the data derived from the additional sensor. In some cases, the processor of the respiratory treatment apparatus may be adapted to couple with a flow sensor, and the additional sensor may be the flow sensor.

Whether in the method, device or respiratory treatment apparatus embodiments, in some cases, the sensor that generates the head strain signal may include any one or more of a strain gauge, a piezoresistor, tensometer, spring guage or other sensors capable of generating a strain signal.

In some cases, the sensor may be configured as a component of headgear. For example, the sensor may be configured to detect changes in tension of one or more straps of the headgear. Still further, the sensor may be configured to detect changes in head or face contact compression with a portion of the headgear. Optionally, the sensor may be a component of headgear for a patient interface for a respiratory treatment apparatus, such as a patient interface having a breathable gas conduit. Still further, the sensor may be a component of a patient interface for a respiratory treatment apparatus, the patient interface comprising a breathable gas conduit. Optionally, the patient interface may include or be a respiratory mask.

By way of further example, some embodiments of the technology may involve a patient interface device for a respiratory treatment apparatus. The patient interface device may include one or more sensors configured to generate a head strain signal. The one or more sensors may be adapted for coupling with a signal interface of a processor of a respiratory treatment apparatus for a detection of respiratory related effort by analysis of the head strain signal. The patient interface device may also be configured to conduct a flow of breathable gas from a flow generator of the respiratory treatment apparatus. Optionally, at least one of the one or more sensors may include a strain gauge. At least one of the one or more sensors may include a piezoresistor. At least one of the one or more sensors may include a tensometer. At least one of the one or more sensors may include a spring gauge.

In some embodiments of the patient interface, at least one of the one or more sensors may be a component of headgear for the patient interface. For example, the sensor(s) may be configured to detect changes in tension of the headgear. Optionally, sensor(s) may be configured to detect changes in tension of straps of the headgear. Still further, the sensor(s) may be configured to detect changes in head or face contact compression with a portion of the patient interface. In some cases, the patient interface may be a respiratory mask and the at least one of the one or more sensors may be a component of the mask.

Various aspects of the described example embodiments may be combined with aspects of certain other example embodiments to realize yet further embodiments.

Other features of the technology will be apparent from consideration of the information contained in the following specification, drawings and claims.

BRIEF DESCRIPTION OF THE DRAWINGS

The present technology is illustrated by way of example, and not by way of limitation, in the figures of the accompanying drawings, in which like reference numerals refer to similar elements including:

FIG. 9 is a right side view of another respiratory treatment mask with a strain sensor integrated in headgear for the nasal mask;

FIG. 10 is a left side view of the respiratory treatment mask of FIG. 9 with an additional strain sensor integrated in the headgear support for the mask;

FIG. 13 illustrates a graph of a flow signal, such as a signal from a flow sensor associated with a nasal cannula;

FIG. 14 is a graph showing several example strain signals from sensors of the present technology on a common time scale and collected in correspondence with the flow signal of FIG. 13;

DETAILED DESCRIPTION

Figure 1:
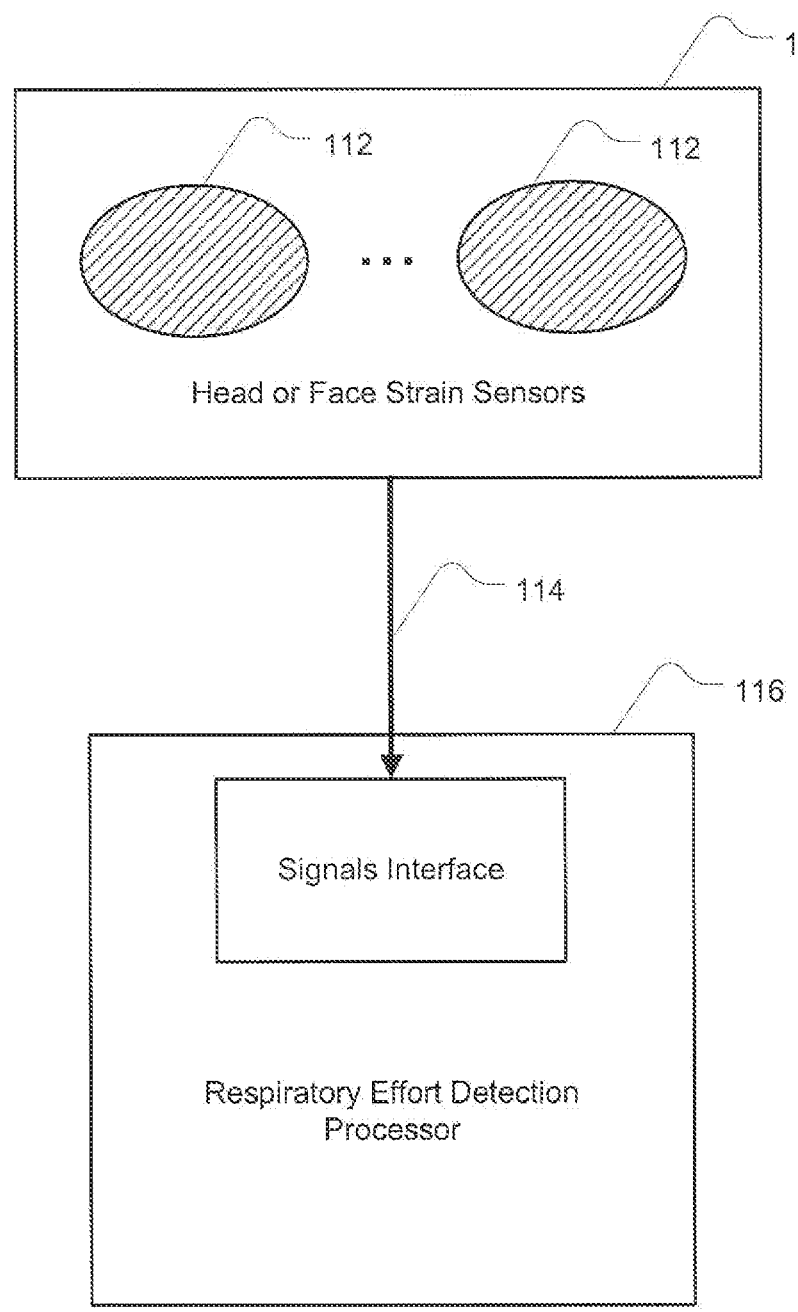
FIG. 1 illustrates example components of a monitoring device to implement respiratory effort detection based on head and/or facial strain sensors.

The present technology involves methods and devices for the detection of head, neck or facial strain signals (for succinctness of reference, any such signals may be referred hereinafter as head signals). Such embodiments of the technology may derive respiratory effort signals based on head or facial strain sensors, which may be further utilized to classify or detect sleep disordered breathing events. As illustrated in FIG. 1, an example of the technology that employs a set of strain sensors 110. The set of strain sensors typically includes one or more head and/or facial strain sensors 112. In some embodiments, such sensors may be configured for generating strain-related electrical signals that may be representative of respiratory related movement of the face, neck or head of a patient.

In the example illustrated in FIG. 1, the sensors may generate the head or facial strain signal(s) 114 for a controller or detection processor 116 of a monitor or other apparatus by communicating the signals in wire leads to the signal interface of a controller or processor. However, in some embodiments, the sensors themselves may be implemented with components for transmitting the strain signals to the controller or detection processor by various forms of communication, including wireless. For example, the signals interface of the detection processor or controller may include a receiver or transceiver to communicate wirelessly with one or more transmitters or transceivers integrated with the sensors. In such a case, data representing the strain signal(s) may be transmitted digitally, for example, by any suitable wireless protocol, such as Bluetooth. Optionally, a set of the sensors may share a common transmitter or transceiver for transmission of the data of several sensors to the controller.

The head strain signal(s) 114 produced by these sensors may then be processed by the detection processor 116 to detect or derive respiratory effort signals and/or to identify or classify sleep disordered breathing events such as classifying central and obstructive apneas or central and obstructive hypopneas. Thus, in some examples of the described technology, the evaluation of head strain signals may serve as a classification of sleep disordered breathing events. Accordingly, a processor may be configured to implement particular methodologies to assess detected sleep disordered breathing events based on the head or facial strain signals and analysis thereof such as by the algorithms described in more detail herein. For example, a device controller or processor may include integrated chips, such as application specific integrated chip(s), a memory and/or other control instruction, data or information storage medium with the methodologies. Thus, programmed instructions encompassing the methodologies may be coded on integrated chips or in the memory of the device. Such instructions may be loaded as software or firmware using an appropriate data storage medium.

Figure 2:
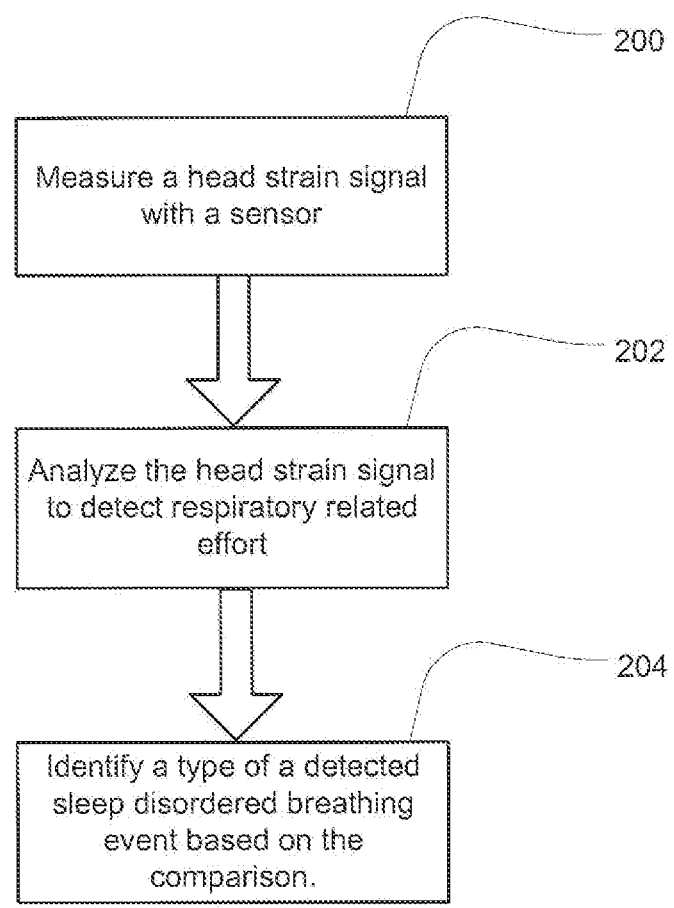
FIG. 2 is an example of a methodology for a controller or processor to detect respiratory effort and/or identify sleep disordered breathing events of the current technology based on strain measurements.

An example methodology for a processor of such an apparatus to assess a head or facial strain signal is illustrated in the flow chart of FIG. 2. At 200, a head or facial strain signal is measured with a sensor. At 202, the head strain signal is analyzed to detect respiratory related effort. Optionally, at 204 a type of a detected sleep disordered breathing event may be determined based on the analysis. For example, the measured head or facial strain signal coincident in time with a detection of flow limitation or a detection of a reduction in a measure of ventilation, may be compared to a threshold chosen to be indicative of movement associated with respiratory related effort. If the comparison indicates the presence of respiratory effort, a sleep disordered breathing event may be characterized as an obstructive event (e.g., an obstructive apnea or obstructive hypopnea). If the comparison indicates the absence of respiratory effort, the sleep disordered breathing event may be characterized as a central event (e.g., a central apnea or a central hypopnea).

Accordingly, typical examples of the current technology may employ suitable sensors that are configured to detect movement of one or more different portions of the head or face to generate the head or facial strain signals. For example, the set of strain sensors may include any one or more, or any combination of, a strain gauge, a piezoresistor, a tensometer, a spring gauge, a force sensitive resistor or similar. The sensors may be mechanical, electrical, magnetic, electromagnetic, pneumatic, optical or any other suitable sensor. As discussed in more detail herein, these sensors may be configured within headgear to ensure positioning of the sensors for detecting strain such as by detecting tension or compression associated with the head or facial movement in relation to the sensors of the headgear. For example, a sensor may be configured to detect tension transferred to one or more straps of the headgear as the face or the neck moves. Alternatively, the sensors may be configured to detect compression such as the force or pressure exerted by the face against a sensor of the headgear. Such sensors may even be configured to detect deformation of a mask component that may be indicative of respiratory related facial movement.

Example Headgear Embodiments

For example, in some embodiments, one or more sensors may be implemented to detect headgear tension or to detect headgear force exerted against the headgear. The sensors may be located on one or more of the straps of the headgear. For example, one or more straps of the headgear may be near the patient's chin and/or mouth and may include sensors, or other headgear tension detection means. Thus, the sensors may detect changes in the position of the patient's chin or mouth as an indication of whether the patient is exerting effort or not, such that the effort may be determined to correspond with respiratory effort. Optionally, all straps of the headgear system may have a headgear detection means. Examples of such embodiments are illustrated in FIGS. 3 and 4.

Figure 3:
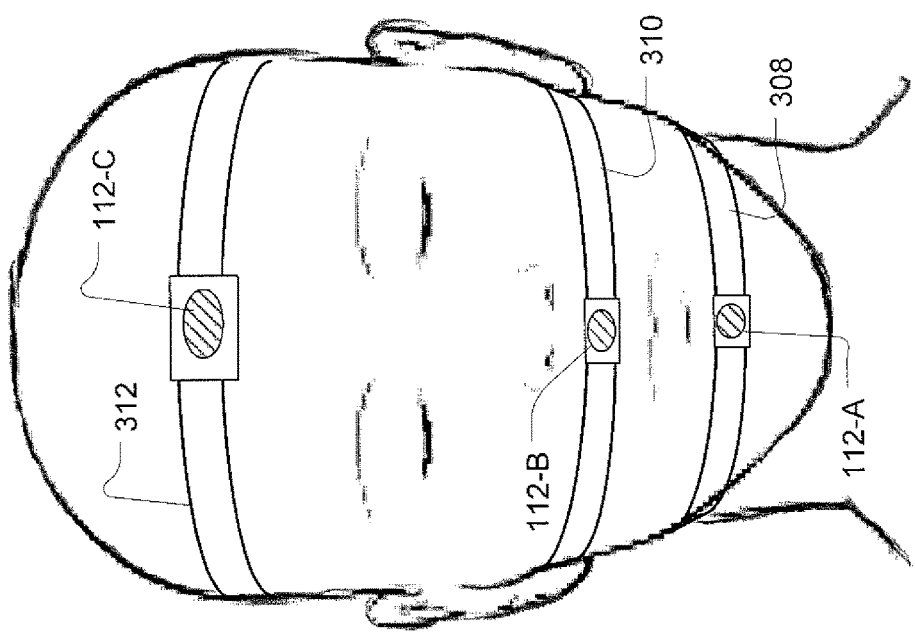
FIG. 3 illustrates example head or facial strain sensors in some embodiments of the present technology.

FIG. 3 shows headgear straps 308, 310 and 312 with sensors 112-A, 112-B and 112-C. Embodiments may include one or more of the headgear straps. In this headgear support, the strain sensor 112-A is located on or integrated in a strap that is proximate to the chin or mouth to detect tension or compression associated with movement of the mouth or chin. Similarly, strain sensor 112-B is located on or integrated in a strap that is proximate to the mouth or nose to detect tension or compression associated with movement of the mouth or nose. Still further, strain sensor 112-C is located on or integrated in a strap that is proximate to the forehead to detect tension or compression associated with movement of the forehead. Patterns of one, some or all of the signals from the strain sensors located to measure strain from different portions of the head or face may then be analyzed to detect efforts associated with respiration or rule out movements that may not be associated with respiration.

Figure 4:
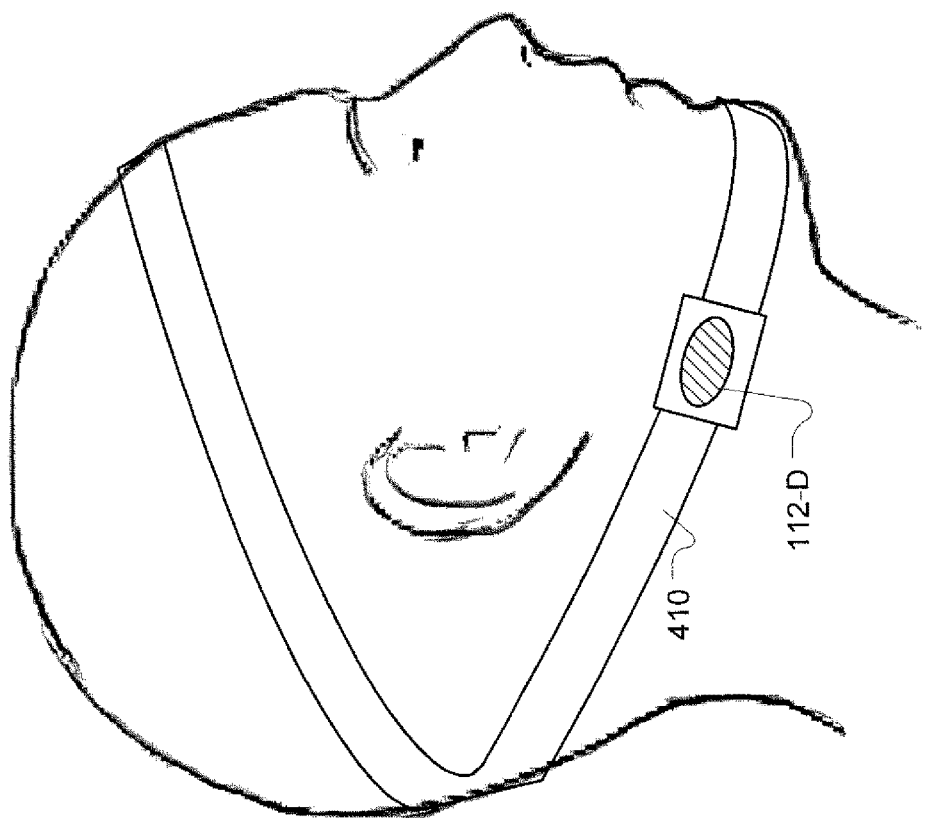
FIG. 4 illustrates additional example head or facial strain sensors in some embodiments of the present technology.

Similarly as shown in FIG. 4, the headgear straps 410 may be implemented to measure head or facial strain signals with stain sensor 112-D. For example, the increased tension associated with the lateral stretching or elongation of the headgear strap 410 caused by movement of the chin due to opening of the mouth may be measured by strain sensor 112-D.

Optionally, the strain sensors may be incorporated into other types of headgear. For example, in some embodiments of the current technology, the sensors may be designed or integrated with additional structures that ensure proper orientation for measurement. In the example case of a respiratory treatment apparatus, the sensors may be embedded, adhered or otherwise integrated with a cushion, cushion surface or frame of a patient interface such as a mask (e.g., a nasal mask, nose and mouth mask, or full face mask), nasal prongs or nasal pillows etc., for a respiratory treatment apparatus (e.g., a CPAP apparatus or ventilator apparatus). Similarly, the sensors may alternatively or in addition thereto, be integrated with headgear, such as a strap of headgear for a patient interface of a respiratory treatment apparatus (e.g., a nasal mask, nasal prongs, nasal pillows or full face mask). Examples of such embodiments are illustrated in FIG. 5 through 10.

Figure 5:
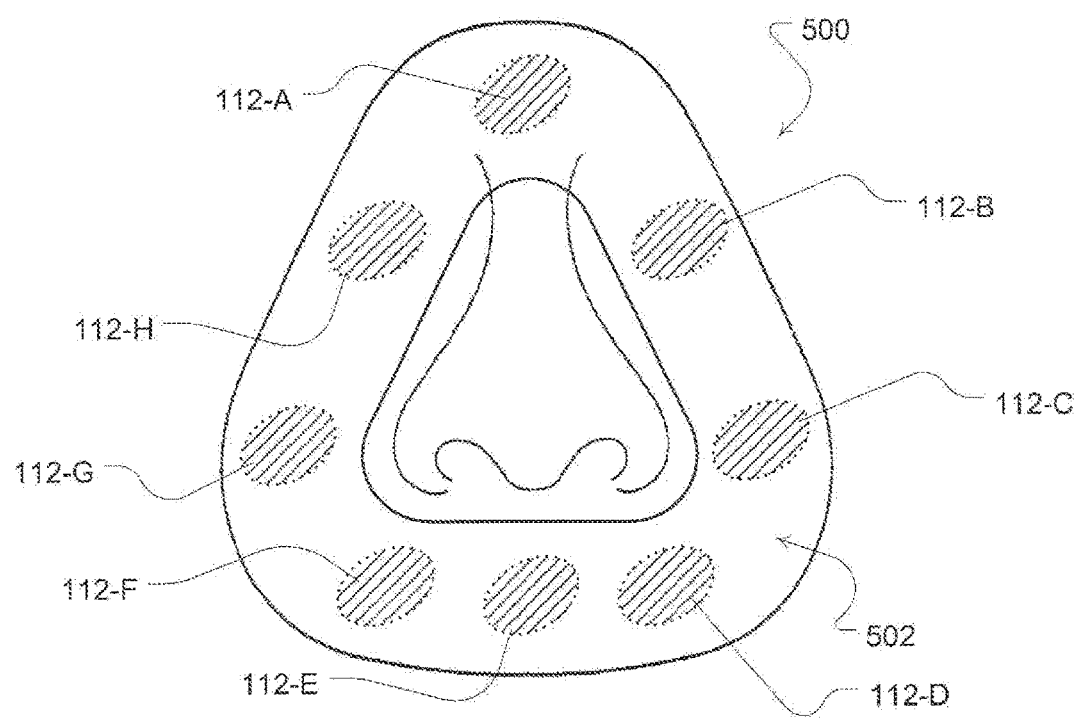
FIG. 5 is an example nasal respiratory treatment mask with integrated strain sensors of the present technology.

In FIG. 5, a nasal mask 500 includes a cushion 502 that when worn may be compressed to the face around a patient's nose for providing a pressure seal for a respiratory pressure treatment such as a CPAP treatment for sleep disordered breathing. Any of sensors 112-A, 112-B, 112-C, 112-D, 112-E, 112-F, 112-G and 112-H may serve as a facial strain sensor. Thus, the sensor may be integrated with the cushion 502 or a mask frame component such that when the cushion is worn, the sensor(s) has a desired orientation or facial/head location. Such sensors may then measure the force or compression associated with the face so that changes in the force or compression indicative of movement due to respiratory effort may be detected. Optionally, the wire leads for the sensors may be routed within or upon a portion of the patient interface or mask so that the leads may extend to electronically couple with a signal interface of a processor described herein, such as a processor of a respiratory treatment apparatus. For example, these leads may also be integrated with a breathable gas or airflow conduit that extends from the patient interface to direct airflow from a flow generator of a respiratory treatment apparatus. Although eight sensors are shown in the example of FIG. 5, it is understood that one or more may be utilized. For instance, in some examples of the mask 600 only a single sensor may be integrated with the mask cushion 502 or mask frame. In such an example any necessary or desired additional sensors may also be integrated on headgear such as described in the examples of FIGS. 3, 4, and 7-10.

Figure 6:
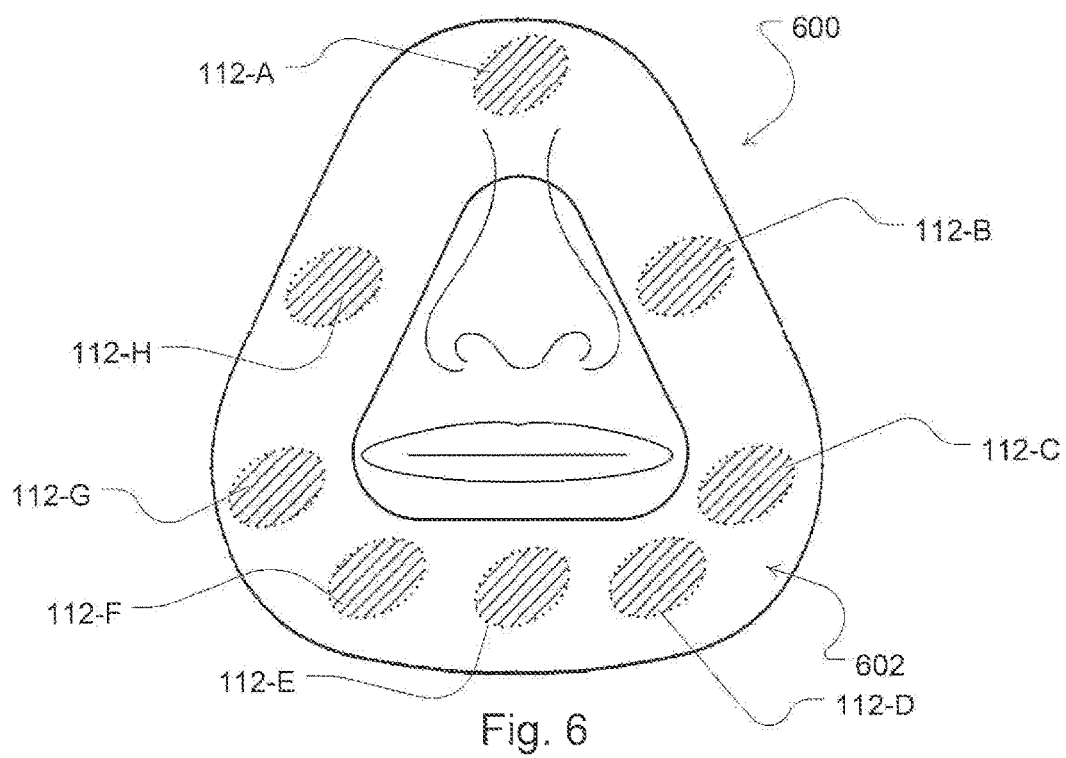
FIG. 6 is an example nose and mouth respiratory treatment mask with integrated strain sensors of the present technology.

FIG. 6 illustrates a nose and mouth respiratory mask 600 to seal airflow or pressure at the nares and mouth of a patient from respiratory treatment apparatus similar to the mask of FIG. 5. In this example, strain sensors 112-A, 112-B, 112-C, 112-D, 112-E, 112-F, 112-G and 112-H are integrated with the mask cushion 602 or mask frame. Similar to the example of FIG. 5, this mask may optionally be equipped with any selection of one or more of the illustrated sensors.

Figure 7:
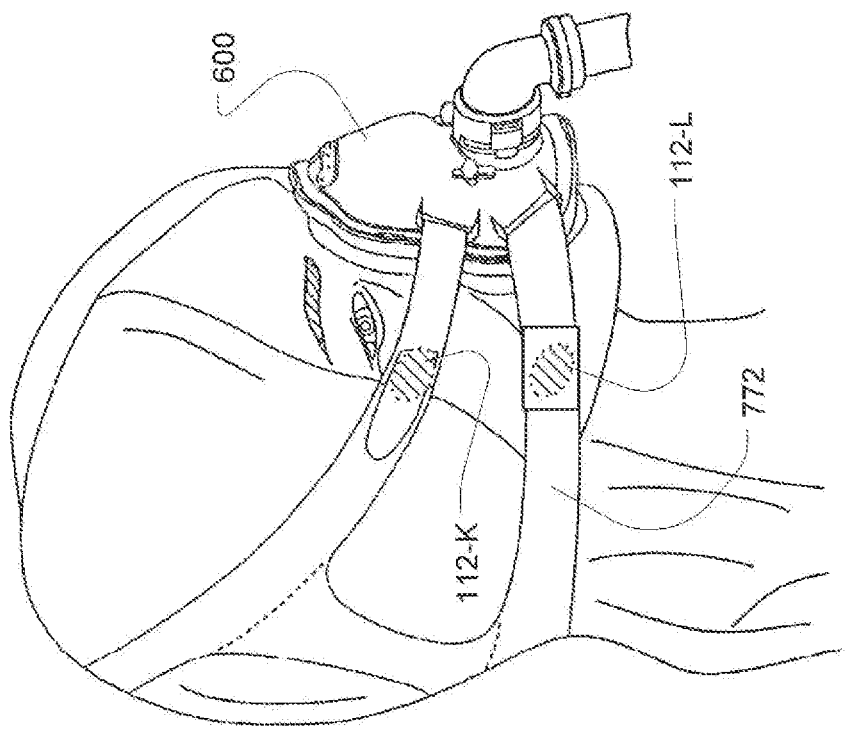
FIG. 7 is a left side view of another respiratory treatment mask with strain sensors integrated in headgear for the mouth and nose mask.
Figure 8:
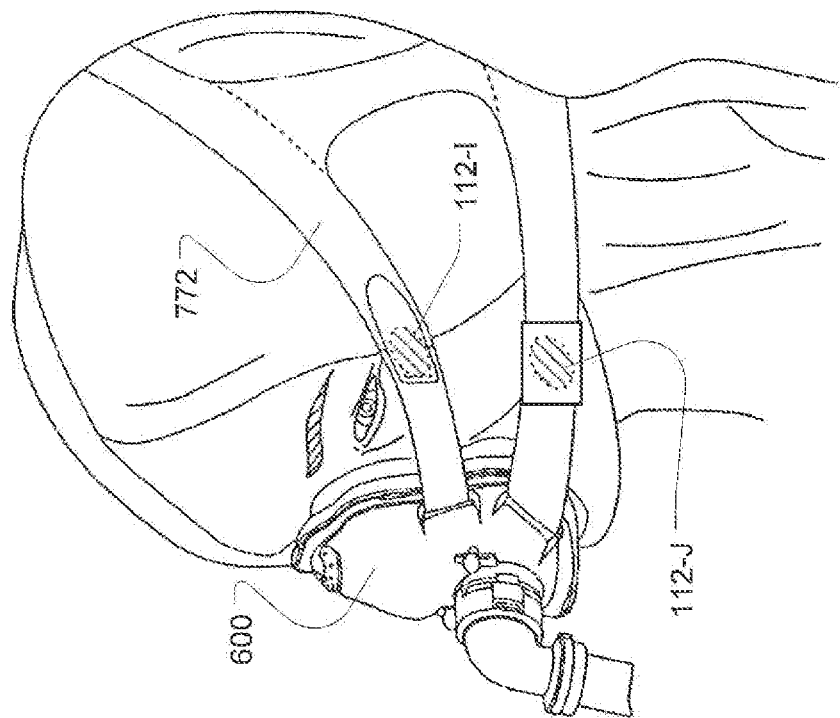
FIG. 8 is a right side view of the respiratory treatment mask of FIG. 7 with optional additional strain sensors integrated in the headgear support for the mask.

FIGS. 7 and 8 depict a mask similar to the mask 600 of FIG. 6. This example employs one or more strain sensors integrated with the headgear support 772 for the mask 600, in addition to or alternatively to the sensors of the mask cushion or frame as shown on mask 600 in FIG. 6. As illustrated in FIGS. 7 and 8, the sensors 112-I, 112-J, 112-K and 112-L may be integrated with a mask strap of the headgear support 772 so that the sensors are in a suitable position for measurement of facial movement when the mask is worn by the patient. In this case, the sensors may detect strain associated with movement of the mouth and/or nose that result in an increase or decrease in the tension of the mask straps by detecting the change in tension of the straps.

Similarly, FIGS. 9 and 10 depict a mask similar to the mask 500 of FIG. 5. This example employs one or more strain sensors integrated with the headgear support 772 for the mask 500, which may be in addition to or alternatively to the sensors of the mask cushion or frame as shown on mask 500 in FIG. 5. As illustrated, sensors 112-I and/or 112-K may be integrated with a mask strap of the headgear support 772 so that the sensors are able to measure strain associated with the movement of the nose and/or upper portion of the mouth. For example, increasing or decreasing tension illustrated along arrows A4 and A1 may be detected with the measurements of sensors 112-I and/or 112-K when the upper portion of the mouth and/or the nose move the mask in association with the patient making some respiratory effort. Similarly, as illustrated, sensors 112-L and/or 112-J may be integrated with a mask strap of the headgear support 772 so that the sensors are able to measure strain associated with the movement of the chin or a lower portion of the mouth. For example, increasing or decreasing tension illustrated along arrows A2 and A3 may be detected with sensors 112-L and/or 112-J when the lower portion of the mouth or chin move in association with the patient making some respiratory effort.

Strain Signal Analysis

In some embodiments, signals of the sensors may be analyzed by a processor. In some such embodiments, the signals may be compared to one or more thresholds which may be chosen or derived to identify movements associated with respiratory effort. For example, in some embodiments a threshold strain value may be determined from the headgear sensors. The threshold headgear strain value may be a measure of the tension or force in the headgear when the patient is at rest without events such as apneas and hypopneas.

Strain measurements may be monitored, such as during a therapy session with respiratory treatment apparatus, and compared to the threshold value. For example, exceeding the threshold may be taken as an indication of headgear or facial movement associated with respiratory effort. Optionally, a delta may be determined such as a difference between the threshold value and a value sampled from the measured strain signal. The delta may be representative of a quantity or degree of head or facial patient respiratory effort. Thus, the value of delta may indicate that the patient is experiencing a respiratory event and a greater delta may indicate events of greater significance and lower delta may indicate events of less significance.

Optionally, the threshold value may be set by a clinician or by the patient. Such a threshold value may be determined at the time that a clinician configures the apparatus for patient use. Still further, threshold values may be empirically determined.

One way of determining the threshold value(s) from the sensors is by measuring strain signals when the patient starts a treatment session for a pre-determined period of time, for example, during a training period on the order of minutes (e.g., to 50 minutes, such as the first 30 minutes of a therapy session.) An average may be taken of the measurements of a headgear sensor during this time, which average may then be taken as a suitable threshold value for the particular sensor. Such a process, which may be controlled by a processor of a respiratory treatment apparatus, may be beneficial since the tension and positioning of the headgear when applied by the patient may be slightly different each time the patient puts on the headgear for a therapy session. Moreover, the tension and flexibility of the headgear may also vary over the headgear life span due to anatomical changes of the patient (e.g., gaining or losing weight), or material degradation of the headgear, etc.

In a further alternative, the threshold attributable to the measurements of any particular sensor may not be a constant value; rather it may be a dynamic value that varies with the patient's normal breathing cycle. For example, the threshold may be a function (e.g., sinusoidal) such that the threshold may increase or decrease in conjunction with detection of the patient respiratory cycle. For example, depending on the type of sensor employed, it may increase during detected periods of expiration or decrease during detected periods of inspiration. Alternatively, the threshold may decrease during detected periods of expiration or increase during detected periods of inspiration. In such embodiments and in the event that an initial training period is implemented, a controller may make the measurements with the sensors in the training period and derive the threshold function by making the strain measurements in correspondence with an automated detection of the phase of patient respiration. For example, averaging of the strain measurements for a dynamic threshold function may be performed with the strain measurements of a certain phase. For example, the measurements from inspiration from several respiratory cycles may be averaged. Similarly, the strain measurements from expiration from several respiratory cycles may be averaged. Thus, different averages may serve as the threshold depending on the particular phase of respiration. Optionally, the respiratory phase may be more finely partitioned than just inspiration and expiration. Any known method for detecting respiratory phase may be employed.

In some embodiments in use with a respiratory pressure treatment apparatus, the thresholds might also vary as a function of pressure settings delivered by the respiratory treatment apparatus. For example, the threshold used for the strain signal comparison may be increased if the strain signals are measured during times of higher pressure settings. Similarly, the threshold may be decreased if the strain signals are measured during lower pressure settings.

Optionally, in some embodiments the strain signals may be filtered. For example, artifact or noise may be removed using a filter or other noise mitigating means.

Further Example Monitoring Embodiments

In one example, the headgear sensors may communicate with a signal interface of a processor of a stand-alone monitoring device or a controller of a flow generator that monitors the sensors, as discussed in more detail herein. Optionally, the sensors may even be configured to communicate with a measurement processor which in turn relays the data collected from the sensors to an analysis processor for signal analysis. However, some embodiments might more simply employ sensors having an indicator or other display (e.g., a mechanical or metered gauge, a light or LCD) for showing information representative of the measurement made by the sensor, whether or not respiratory effort is detected by the measurement, and/or the degree of the respiratory effort. For example, the sensor of the headgear may have a mechanical gauge, markings or other meter that shows the current measurement. Similarly, the sensor of the headgear may have a light that is activated when a signal of the sensor exceeds the threshold. Still further, the sensor of the headgear may have an integrated LCD display that shows the measurement of the sensor, the results of the comparison with the threshold and/or the delta previously discussed.

In the case of a sensor that is configured to simply display a reading or measurement, a clinician may then consider the significance of the reading by reference to a previously determined threshold(s). For example, a current reading of the headgear tension may be compared to a graph of thresholds. Such a graph may show thresholds that vary in correspondence with particular times in the phases of the patient's breathing cycle. Thus, the graph may be used to identify a threshold that depends on the time in the patient's respiratory cycle that the measurement of the sensor was made.

SDB Event Detection/Classification

As previously discussed, the information from the sensors may be employed to indicate or identify events such as Sleep Disordered Breathing (SDB) events in some detector embodiments. Example methodologies for the detection of breathing related events or SDB events may be considered as follows.

(1) Apnea with Effort

An apnea with effort occurs when the patient is experiencing a cessation of breathing while their body is trying to breath by exerting effort. This effort can be flexing of the chest walls, head and/or neck. An apnea with effort may be an obstructive apnea.

This effort may be detected, for example, via the tension of the headgear, as the measurement of the strain sensors increases above a threshold value. For example, as the patient exerts effort, they may move their chin away from their neck. Such movement may increase the tension in, or the force against, the headgear or headgear straps and thereby increase the measure of one or more strain sensors.

A comparison of the strain measure (e.g., headgear tension measurement) with the threshold value, such as in a processor may then serve as a basis for identifying an apnea as an apnea with effort. A cessation of breathing, such as one that is indicative of an apnea, may be determined from an analysis of a patient flow signal by any known methodology. One such methodology may include detecting a cessation of patient respiratory airflow. For example, an apnea condition may be detected by the methods described in U.S. Pat. No. 7,730,886 and/or U.S. Pat. No. 6,675,797, the disclosures of which are incorporated herein by reference. Then, if the headgear tension detected is greater than the threshold value an apnea with effort may be occurring. Thus, the detection of the effort and the coincident apnea may serve as a methodology for an automated classification of an apnea as an obstructive apnea.

In some embodiments, when an apnea with an effort is detected, the monitor or detector may send a signal to an alarm system to alert the patient or clinician. For example, the alarm may be audible or may be logged and reported, e.g., remotely, to the patient or clinician after therapy has ceased.

Optionally, if an apnea with effort is detected based on the strain signal, the detection may serve as a further basis to control a treatment variable change, the variable being one of pressure, flow or ventilation. For example, a respiratory treatment apparatus may increase the pressure being output by a flow generator based on the detection.

In some embodiments, the magnitude of the effort may also indicate what type of event the patient is having. Thus, a patient with an obstructive apnea may exert more effort than a patient with Cheyne Stokes breathing. For example, based on the assessment of different thresholds (e.g., one attributable to Cheyne Stokes detection and another attributable to obstructive apnea) the detection of cessation of respiratory airflow in conjunction with the assessment or the strain signal(s) may serve as a basis to distinguish the two. Optionally, this determination may be based on analysis of the significance of the delta previously described.

(2) Apnea with No Effort

An apnea with no effort is said to occur when the patient is experiencing a cessation of breathing and their body is not trying to initiate breathing as it is not exerting any effort. This may be considered a central apnea.

With no effort, the measurements of the set of sensors (e.g., tension of the headgear) may remain unchanged from the threshold value or not satisfy the threshold. Thus, when an apnea is detected (e.g., by detecting a cessation of breathing in the flow signal), the absence of significant effort by a threshold comparison may serve as a basis to identify the apnea as a central apnea.

It has to be noted that often the so called "mixed" apnea occurs, which represents a combination of an obstructive and central apnea.

In order to facilitate the identification of the specific type of apnea occurring, a headgear tension measurement means may measure the headgear tension and send the tension data to a detection processor. The processor may compare this measured strain signal against the threshold value, and if, for example, the headgear tension detected is the same as the threshold value, the apnea may be characterized as an apnea without effort. Optionally, this identification of the detector may also be based on further input. For example, the detector may also determine if the patient's airway is open or not by further analysis of a forced oscillation process and/or a cardiogenic airflow process. The processor may then determine if the patient is having an apnea with no effort (e.g., a central apnea), if (a) the patient's respiratory airflow has ceased; and (b) the airway is open, and/or (c) the headgear strain measurement is unchanged or insignificant.

Optionally, if an apnea without effort is detected, the detector may send a signal to an alarm system to alert the patient or clinician. The alarm may also be audible or may be logged and reported, e.g., remotely, to the patient or clinician after therapy has ceased.

In some embodiments, such as in the case that the detector is part of, or communicates with, a respiratory treatment apparatus, the detection of the apnea without effort based on the strain measurement, may serve as a basis for a controller of the respiratory treatment apparatus to reduce a treatment variable, such as pressure, flow or ventilation, being generated by the flow generator.

(3) Hypopnea with Effort

In some embodiments, analysis of the strain measure may serve as a basis for a detector to identify an obstructive hypopnea. A hypopnea may be considered a partial reduction in breathing that lasts a short period of time, e.g., at least 10 seconds during sleep. Examples of hypopnea detection methodologies are described in U.S. patent application Ser. No. 12/781,070, filed May 17, 2010, the disclosure of which is incorporated herein by reference. By analysis of a measured flow signal, a detector may detect a condition indicative of hypopnea. For example, a reduction in a measure of ventilation, based on the flow, for a period of time may be taken as an indication of hypopnea. Such an indication of hypopnea that is coincident in time with a significant measure of the strain sensors previously described, may be taken as an indication of a hypopnea with effort or an obstructive hypopnea. For example, if a comparison of one or more strain measures with a threshold(s) indicates that head or facial effort is being made, a detector may score or identify the detected hypopnea as an obstructive hypopnea.

Optionally, if an obstructive hypopnea is detected, the detector may send a signal to an alarm system to alert the patient or clinician. The alarm may also be audible or may be logged and reported, e.g., remotely, to the patient or clinician during the therapy or after therapy has ceased.

In some embodiments, such as in the case that the detector is part of, or communicates with, a respiratory treatment apparatus, the detection of the obstructive hypopnea based on the strain measurement, may serve as a basis for a controller of the respiratory treatment apparatus to change (e.g., increase) a treatment pressure being generated by the flow generator. By controlling the treatment pressure, one can modulate the ventilation (and the flow) and keep the airway open. Alternatively, the apparatus may be configured to directly control not the pressure, but the flow or the ventilation.

(4) Hypopnea with No Effort

In some embodiments, analysis of the strain measure may serve as a basis for a detector to identify a central hypopnea. For example, a reduction in a measure of ventilation, based on the flow, for a period of time may be taken as an indication of hypopnea. Such an indication of hypopnea that is coincident in time with no significant measure of strain being detected by the strain sensors, may be taken as an indication of a hypopnea without effort or a central hypopnea. For example, if a comparison of one or more strain measures with a threshold(s) indicates that head or facial effort is not being made, a detector may score or identify the detected hypopnea as a central hypopnea.

Optionally, if a central hypopnea is detected, the detector may send a signal to an alarm system to alert the patient or clinician. The alarm may also be audible or may be logged and reported, e.g., remotely, to the patient or clinician during the therapy or after therapy has ceased.

In some embodiments, such as in the case that the detector is part of, or communicates with, a respiratory treatment apparatus, the detection of the central hypopnea based on the strain measurement, may serve as a basis for a controller of the respiratory treatment apparatus to change (e.g., decrease) a treatment pressure being generated by the flow generator. Optionally, the apparatus may be configured to control any combination of the pressure, the flow and/or the ventilation of such a treatment apparatus.

(5) Respiratory Effort Related Arousal (RERA)

In some embodiments, the strain sensors may be implemented for a detection of respiratory effort related arousal (RERA) events. For example, if the measurements of the strain sensors detect an increasing level of effort, such as a continuous increase or several increases in the measure during a period of time (e.g., over the course of about a minute or two), a RERA may be identified as occurring. Optionally, in some embodiments the detection or identification of a RERA event based on the strain measurements may be further conditioned on data from other sensors. For example, if an analysis of respiration data, such as a measure of respiratory flow from a flow sensor or other respiration signal from a respiration sensor, indicates the occurrence of a RERA and an analysis of the signal from the strain sensor described herein indicates the occurrence of a RERA, the combined detections may be taken as a RERA event occurring and the RERA event may be scored by a detection device. In such an example, if either the strain signal based analysis or the flow sensor based analysis does not indicate a RERA event, then no RERA event would be scored. Thus, the RERA event would be conditioned on a positive detection analysis of data or signals from both the flow sensor and the strain sensor. In one such example, the flow based RERA detection methodologies described in PCT/AU2010/000894 filed on Jul. 14, 2010, which is incorporated herein by reference, may be implemented. However, other respiration or flow based RERA detection methodologies may also be implemented.

Combination with Other Detectors

A The strain and/or headgear detection methodologies may be utilized in combination with other SDB detection devices. For example, as previously mentioned, it may be implemented with apparatus for controlling a forced oscillation process or a cardiogenic signal detection process. It may also be implemented with other apnea or hypopnea detection devices and methods to assist the detector in determining if a detected apnea or hypopnea is with effort or without effort.

Furthermore, the strain and effort detector described herein may also assist in determining a pattern of effort and no effort events throughout therapy. Based on the detection of such a pattern, the detector may determine if a patient is at risk of cardiovascular disease. For example, if the detector determines a certain number of central events during a treatment session or a particular time period, a warning or message may be generated to warn a user or physician of such an increased risk. For example, the AASM guidelines define the central sleep apnea syndrome as requiring a central apnea index of greater than or equal to 5 apneas per hour.

Example Respiratory Treatment Apparatus

Figure 11:
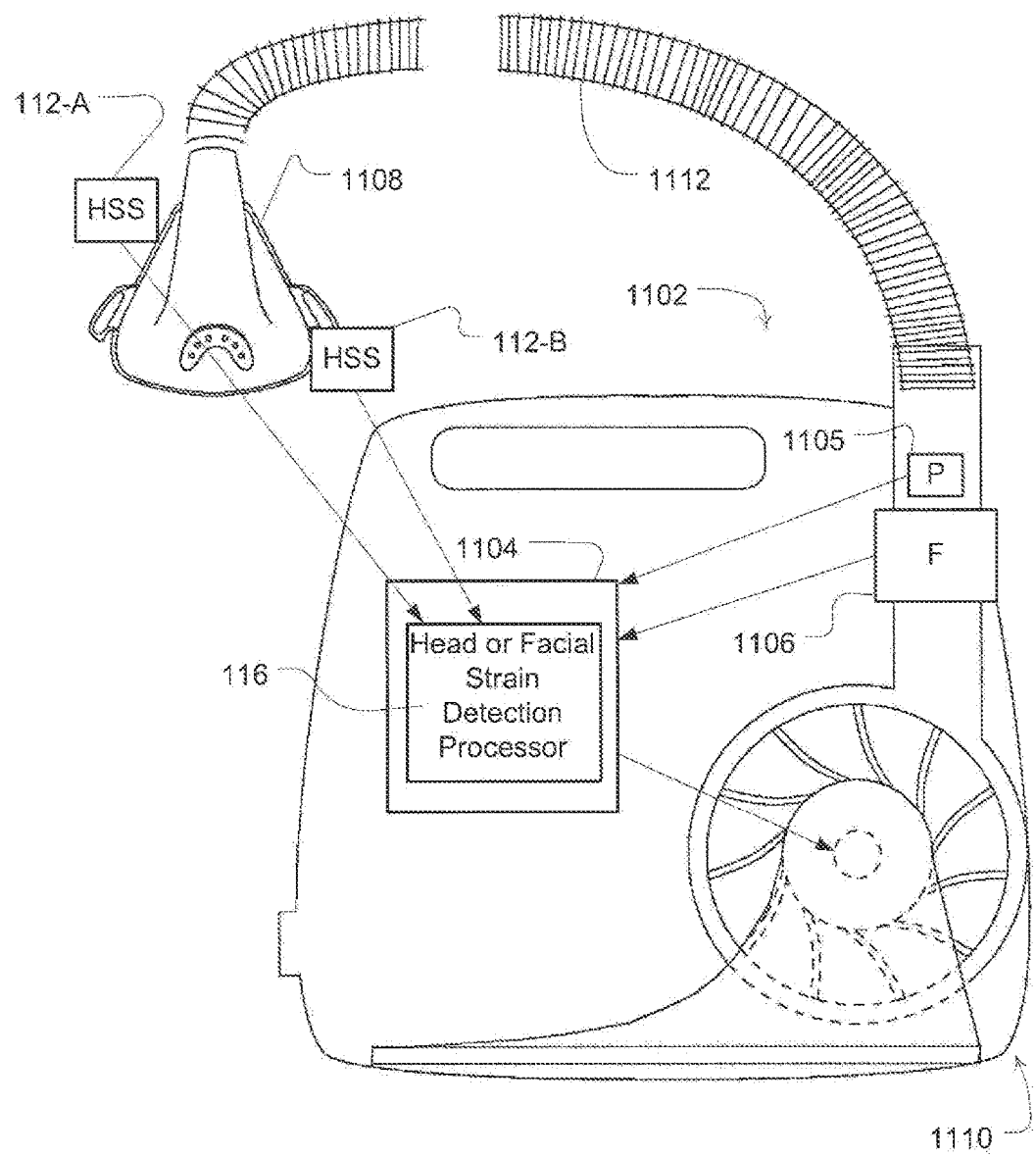
FIG. 11 is an example respiratory treatment apparatus with head or facial strain sensors and a controller having a head or facial strain signal detection processor of the present technology.

While the technology of the detection processing may be implemented as a stand-alone monitoring device as previously discussed, the technology may also be combined with other devices such as a respiratory treatment apparatus. FIG. 11 illustrates an example respiratory treatment apparatus that may implement the sensors and methodologies described herein.

In reference to FIG. 11, the respiratory treatment apparatus 1102 may include an attachable patient interface, such as the mask 1108 and gas delivery tube or conduit 1112. In such a device, the delivery tube 1112 may serve as a conduit for leads of the head strain sensor (HSS) 112-A and/or 112-B. The head or facial strain detection processor 116 may then be incorporated with a controller 1104 of the respiratory treatment apparatus 1102. The apparatus 1102 with the controller 1104 may also be configured to provide a respiratory pressure treatment from a flow generator such as a servo-controlled blower 1110. In such a case, the apparatus may optionally include a pressure sensor 1105, such as a pressure transducer to measure the pressure generated by the blower 1110 and generate a pressure signal p(t) indicative of the measurements of pressure.

The respiratory treatment apparatus 1102 may also optionally include a flow sensor 1106 that may be coupled with the patient respiratory interface. The flow sensor generates a signal representative of the patient's respiratory flow. For example, flow may be measured using a pneumotachograph and differential pressure transducer or similar device such as one employing a bundle of tubes or ducts to derive a flow signal f(t).

The signals from the sensors (e.g., flow, pressure and strain) may then be sent to the controller 1104. Optional analog-to-digital (A/D) converters/samplers (not shown separately) may be utilized in the event that supplied signals from the sensors are not in digital form and the controller is a digital controller.

Based on flow f(t) and pressure p(t) signals, the controller 1104, having one or more processors, can generate blower control signals. For example, the controller may generate a desired pressure set point and servo-control the blower to meet the set point by comparing the setpoint with the measured condition of the pressure sensor. Thus, the controller 1104 may make controlled changes to the pressure delivered to the patient interface 1108 by the blower 1110. Optionally, such changes to pressure may be implemented by controlling an exhaust with a mechanical release valve (not shown) to increase or decrease the exhaust while maintaining a relatively constant blower speed. With such a controller or processor, the apparatus can be used for many different pressure treatment therapies, such as the pressure treatments for sleep disordered breathing, Cheyne-Stokes Respiration or obstructive sleep apnea (e.g., CPAP, APAP, Bi-Level CPAP, Auto-VPAP, etc.) by adjusting a suitable pressure delivery equation. Optionally, the controller 1104 may also be implemented to make changes to pressure treatment based on detected changes of the metrics or detected events derived from the head or facial strain signal as previously discussed.

The controller may optionally include a display such as one or more warning lights (e.g., one or more light emitting diodes). The display device may also be implemented as a display screen such as an LCD. Optionally, the display device may be controlled to show data derived from the strain signals, such as the determined facial effort, the identified sleep disordered breathing events and/or the warnings previously described. Optionally, strain signal(s) may be displayed on a graph of the display.

In some embodiments, the respiratory treatment apparatus may be configured as a noninvasive ventilation (NIV) apparatus that delivers a treatment pressure or ventilation in synchrony with detected patient respiration (e.g., a bi-level pressure treatment having a synchronized inspiratory positive airway pressure level (IPAP) and expiratory positive airway pressure level (EPAP)). Optionally, a mask or headgear for the device may be configured with the strain sensors and the controller of the apparatus may be implemented to analyze the signals therefrom to detect apparatus asynchrony such as a missed triggering event. Such an event may occur when the patient initiates inspiration but the apparatus fails to change to the IPAP level from the EPAP level. Such an event may be detected, for example, when the signal of the strain sensors indicates a level of increased effort suggestive of inspiration but the apparatus remains in an EPAP state.

In a further example respiratory treatment apparatus, detection of sleep disordered breathing events, such as apnea or hypopnea, by a controller or processor of the apparatus may be based on the analysis of the head strain signal, such as those previously described, and a further analysis of signal(s) of further sensor(s) (e.g., a flow sensor, pressure sensor, respiration sensor, etc.). Based on such a combined analysis that detects a treatable SDB event, a processor controlling the analysis may then make a change to the treatment pressure. For example, if an obstructive apnea is detected from an analysis of data from a flow sensor and the head strain signal, treatment pressure may be increased. By way of a further example, if a central or mixed apnea is detected from an analysis of data from a flow sensor and the head strain signal, treatment pressure may be maintained or decreased. By way of a further example, if an obstructive hypopnea is detected from an analysis of data from a flow sensor and the head strain signal, treatment pressure may be increased. Still further, if central or mixed hypopnea is detected from an analysis of data from a flow sensor and the head strain signal, a treatment pressure may be maintained or decreased.

Example Controller Architecture

Figure 12:
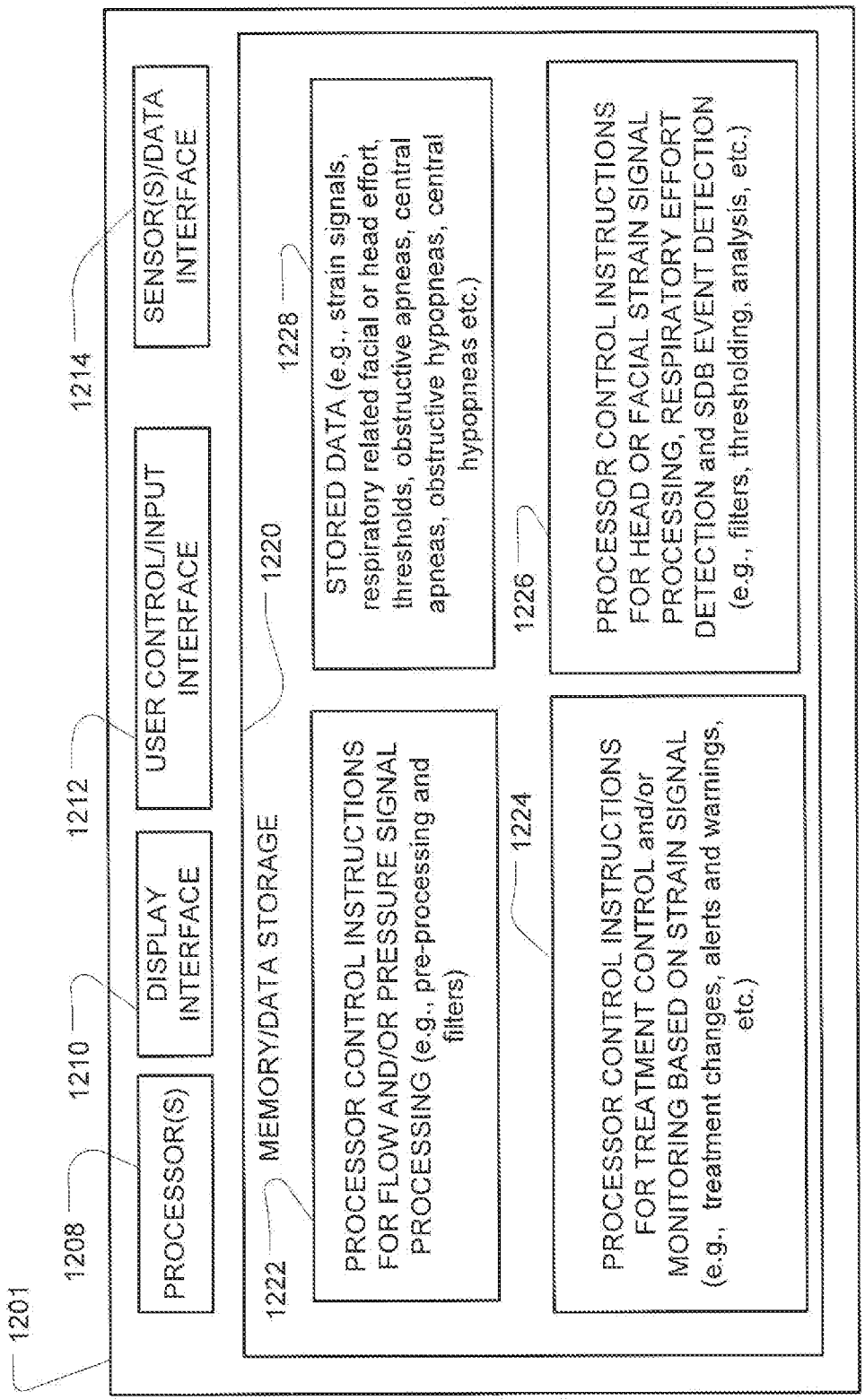
FIG. 12 is an example controller of a detector for processing head or facial strain signal(s) in some embodiments of the present technology.

An example system architecture of a controller suitable for the present technology is illustrated in the block diagram of FIG. 12. In the illustration, the controller 1201 for the head or facial strain detection processor 116 that may be part of, or independent from, the respiratory treatment apparatus 1102 may include one or more processors 1208. The system may also include a display interface 1210 to output event detection reports (e.g., central apnea, obstructive apnea, central hypopnea, obstructive hypopnea, facial related respiratory effort, etc.), results or graphs (e.g., strain or effort signals, etc.) or warnings as described herein such as on a monitor or LCD panel. A user control/input interface 1212, for example for a keyboard, touch panel, control buttons, mouse etc. may also be provided to activate or modify the control methodologies described herein. The system may also include a sensor or data interface 1214, such as a bus, for receiving/transmitting data such as programming instructions, pressure and flow signals, strain signals, etc. The device may also typically include one or more memory/data storage components 1220 containing control instructions of the aforementioned methodologies (e.g., FIG. 2). These may include processor control instructions for flow and/or pressure signal processing (e.g., pre-processing methods, filters) at 1222. These may also include processor control instructions for treatment control and/or monitoring based on strain signal measurement (e.g., treatment changes, alerts and warnings, etc.) at 1224 as discussed in more detail herein. They may also include processor control instructions for head or facial strain signal measuring and processing, respiratory effort detection and SDB event detection (e.g., filtering, thresholding, analysis, apnea detection, hypopnea detection, etc.) at 1226. Finally, they may also include stored data 1228 associated with executing, or processing the data obtained by, these methodologies such as head or facial strain signals, respiratory related facial or head effort signals, obstructive apneas, central apneas, obstructive hypopneas, central hypopneas, thresholds, etc.).

In some embodiments, these processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

Example Signal Processing of Head Strain Signals

Figure 15:
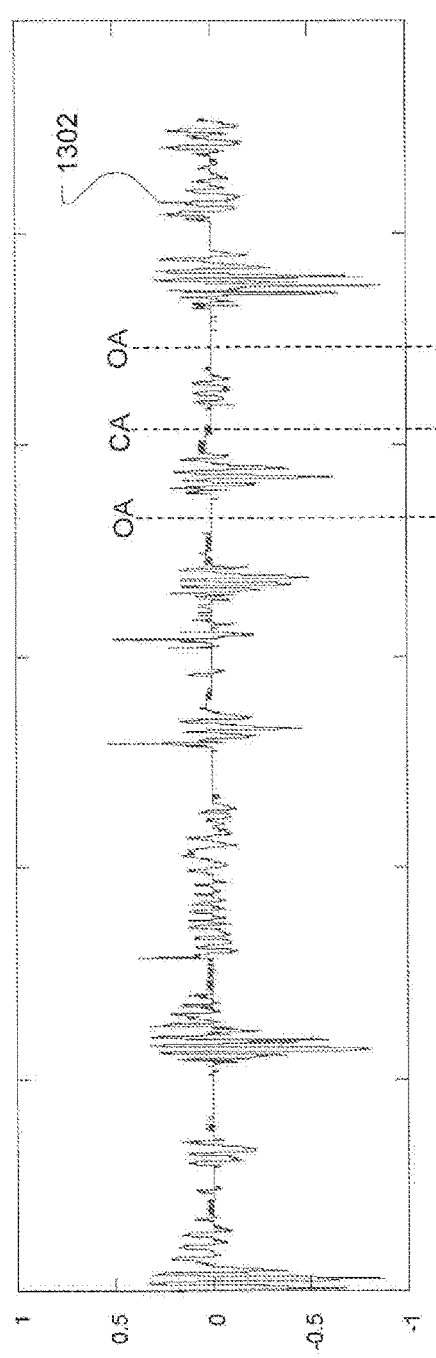
FIG. 15 is a graph of the flow signal of FIG. 13 showing several sleep disordered breathing events.
Figure 16:
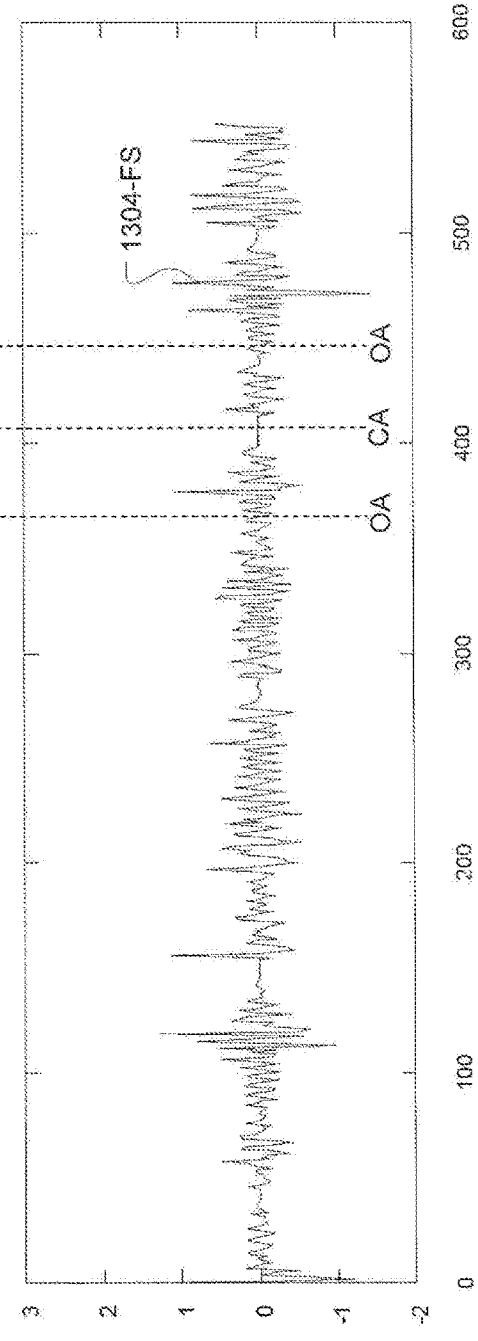
FIG. 16 is a graph of a head strain signal of FIG. 14 after application of a filtering process.

FIGS. 13-19 show example signals that may be generated in some processing embodiments as previously described that may implement a classification of sleep disordered breathing events based on one or more head strain signals. For example, in FIG. 13 a flow signal is plotted during a period of time (0-600 seconds), such as by recording an output signal from a flow sensor coupled to a nasal cannula. The flow signal includes several sleep disordered breathing events which are labeled in FIG. 15 as obstructive apnea OA and central apnea CA. During this time frame, head strain signals may be generated by sensors of the present technology, such as the sensors illustrated in FIG. 4. The sensors may, for example, be located on headgear on opposing sides of a patient's jaw or other similar symmetric, or asymmetric, facial or head sensor orientation. For example, the left and right head strain signals 1304-LS and 1304-RS shown in FIG. 14 may respectively be generated from symmetrical left and right head strain sensors. In this graph, the amplitude over time of the head strain signals is plotted in units of Newtons. Head stain signals from multiple sensors may be combined, such as by addition or sum. Such a combined head strain signal 1304-TS, representing the sum of the left and right head strain signals 1304-LS and 1304-RS, is also plotted on the same time scale in FIG. 14. Optionally, as shown in FIG. 16, the combined head strain signal 1304-TS may be processed or filtered to produce a filtered total head strain signal 1304-FS. Such processing may be implemented to remove offset and/or for signal smoothing. As illustrated in FIGS. 15 and 16 at line CA, an absence of significant jaw effort in signal 1304-FS substantially coincides in time with a detected reduction in airflow (e.g., a period of low or no flow longer than about 10 seconds) represented in the flow signal 1302. The combination of low, or zero, flow signal with an absence of jaw effort may be taken as a condition that indicates a central apnea event. However, at line OA, a detected reduction in airflow (e.g., a period of low or no flow longer than about 10 seconds) represented in the flow signal 1302 is substantially coincident in time with the presence of some significant jaw effort This may be taken as a condition that indicates an obstructive apnea event. In this example, filtering to produce the filtered total head strain signal 1304-FS may be accomplished with a high pass filter, such as a 2-pole Butterworth filter with a 3 db frequency of 0.125 HZ. However, other filters may be implemented.

Processing of the head strain signals may be implemented for the automated detection of the aforementioned presence or absence of significant head or jaw effort, which in turn may serve to qualify the type of apnea. For example, an historic threshold signal may be derived from processing of the strain signals that may be implemented in a comparison with a more recent state of the strain signal for a detection process. Such signals may be considered in the examples of FIGS. 17, 18 and 19.

Figure 17:
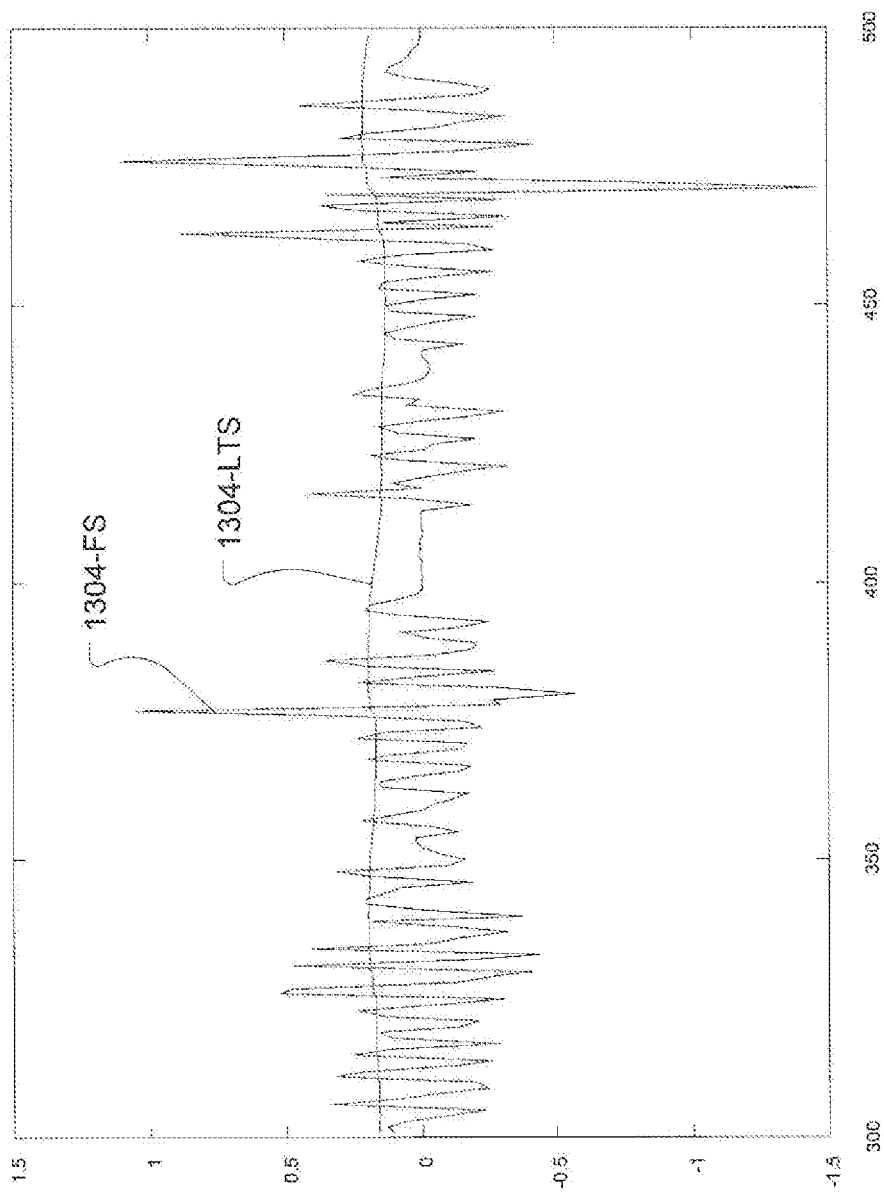
FIG. 17 is a graph showing a portion of the signal of FIG. 16 and a first filtered version of the signal.
Figure 18:
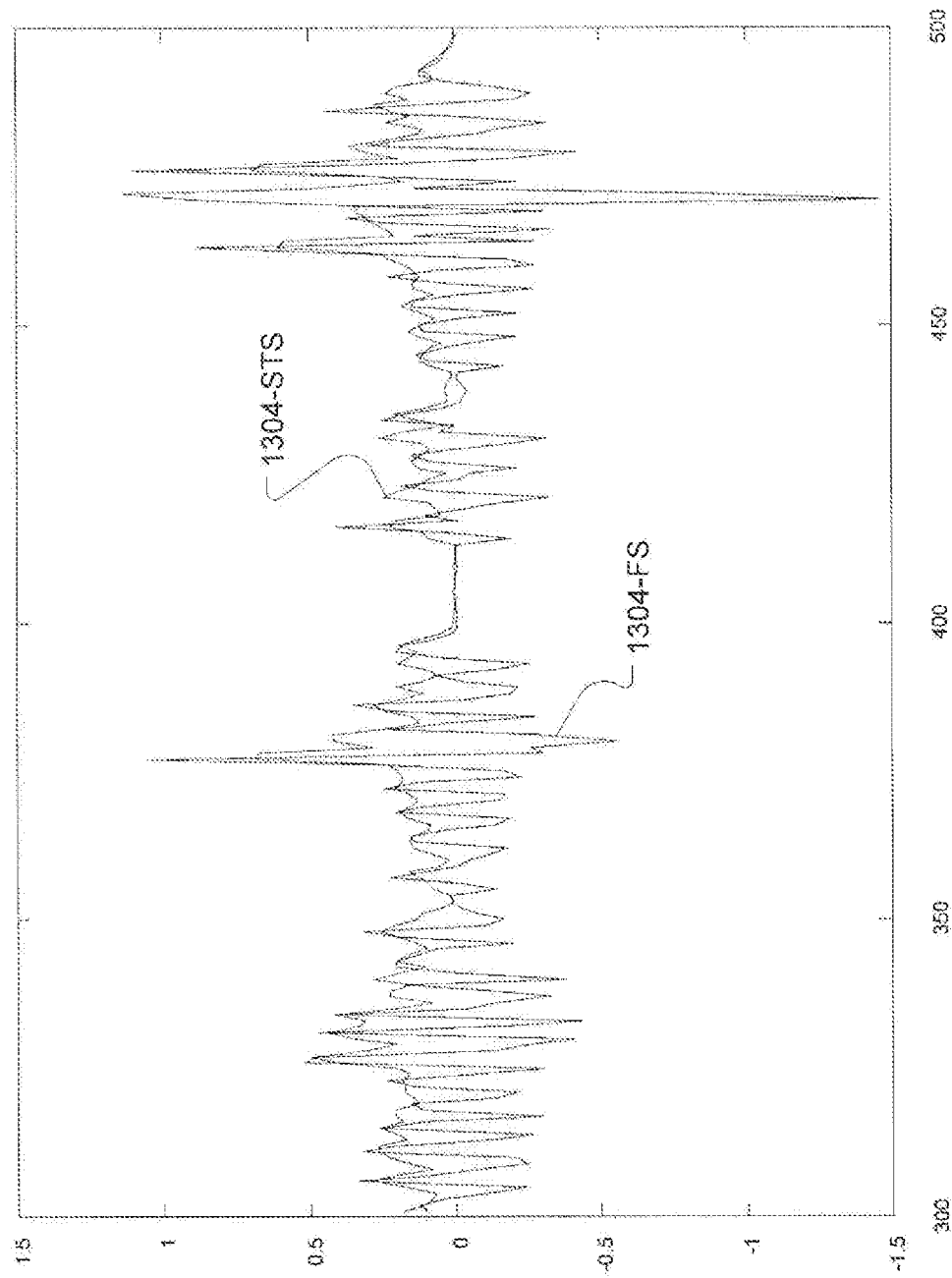
FIG. 18 is a graph showing the same portion of the signal of FIG. 16 and a second filtered version of that signal.

As shown in FIG. 17, the filtered signal 1304-FS may be applied to a further filter, such as a low pass filter, for example, to produce a long-term absolute average signal 1304-LTS. Such a signal may be produced by low pass filtering the absolute value of signal 1304-FS with a long term time constant. A suitable time constant may be on the order of approximately minutes (e.g., about 60 seconds). Similarly, as shown in FIG. 18, the filtered signal 1304-FS may be applied to a still further filter, such as a low pass filter or variance filter, for example, to produce a short-term absolute average signal 1304-STS. Such a signal may be produced by low pass filtering the absolute value of signal 1304-FS with a short term time constant. A suitable time constant may be on the order of approximately seconds (e.g., about 2 seconds).

Figure 19:
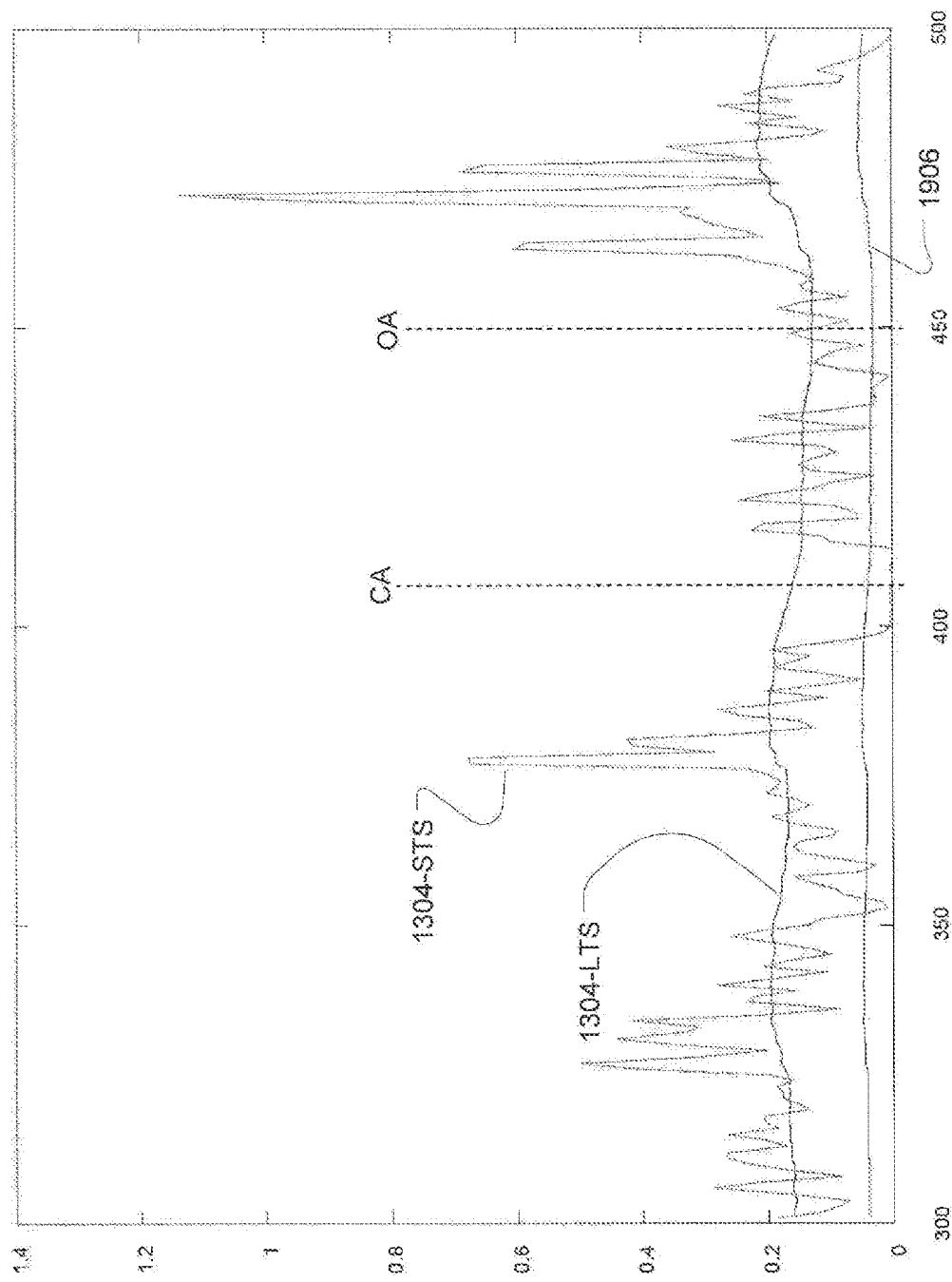
FIG. 19 is a graph of the first and second filtered versions of the signal of FIG. 16 along with a threshold signal derived from one of the first and second filtered versions.

Such signals may then be compared to detect the presence or absence of significant head strain. Signals suitable for such a comparison in some embodiments are illustrated in FIG. 19. In this graph of FIG. 19, the long term strain signal 1304-LTS and the short term strain signal 1304-STS are plotted along with a threshold signal 1906. In this case, the threshold signal may be derived from the long term signal. For example, the threshold signal may be a proportion of the long term signal. A suitable proportion may be a percentage such as a percentage in the range of 5%-50%. In the example, the threshold signal represents approximately 25% of the long term signal.

With such signals an absence of significant head strain may be detected if the short term signal falls below the threshold signal. Optionally, a presence of significant head strain may be detected if the short term signal is at or above the threshold signal. FIG. 19 shows the signals on the same time scale as the flow signal of FIG. 15. As illustrated in FIG. 19, the absence of significant head strain combined with a reduced flow may be indicative of a central apnea event CA, whilst the presence of significant head strain during a reduced flow is indicative of an obstructive apnea event OA. Thus, the effort indicated by the head strain signal may be implemented as a respiratory related indicator such as for distinguishing between central or obstructive events.

In some embodiments of an apparatus, steps for automated processing, such as by a controller or processor, of the head strains signals for detection of head strain, that may then be implemented to characterize a respiratory event, may be summarized as follows:

generate a head strain signal with a head strain sensor;
generate first and second filtered head strain signals based on the generated head strain signal;
make a comparison based on the first and the second filtered signals;
generate an indicator of a presence or absence of significant respiratory effort based on the comparison.

In some implementations, the comparison may include comparing the second filtered head strain signal with a proportion of the first head strain signal. Alternative arrangements may include comparing other functions of the first head strain signal with the second signal or functions thereof, or using functions of the second signal and comparing them with the first signal, or functions thereof.

In some such cases, the first filtered head strain signal may be a long term average head strain signal, such as a long term absolute average. In still further cases, the second filtered head strain signal may be a short term average head strain signal. In some embodiments, such an indication of significant head strain may serve to classify an apnea or a hypopnea as an obstructive event. In some embodiments, such an indication of an absence of a significant head strain may serve to classify an apnea or a hypopnea as a central event. In some such embodiments, first and second filtered head strain signals may be derived from a plurality of head strain signals. In some such cases, the signals may be derived from a combined head strain signal, such as a signal representing a sum of multiple head strain signals.

Figure 20:
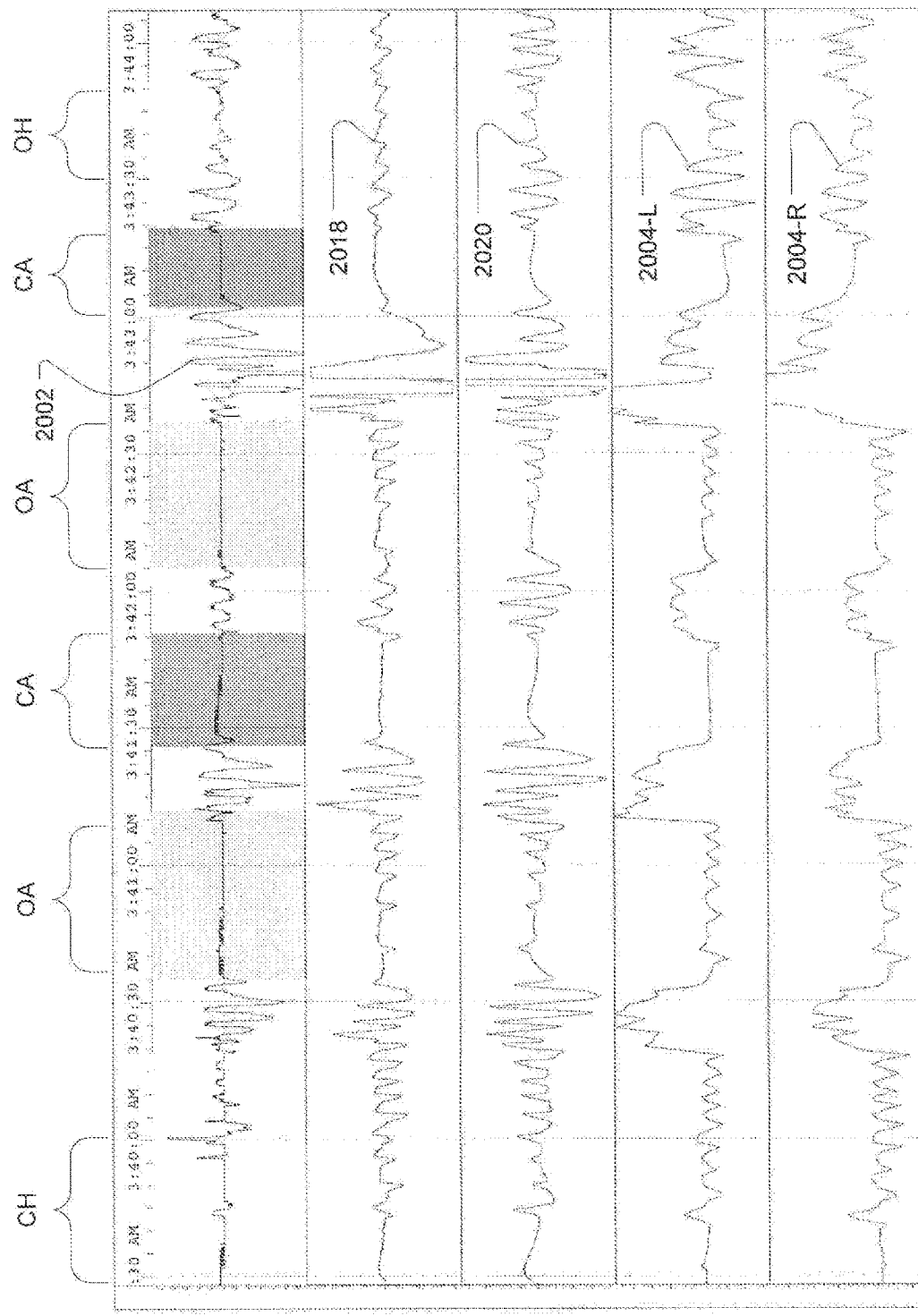
FIG. 20 shows a graph of some head strain signals generated by sensors of the present technology in association with signals from other effort sensors including a thoracic effort sensor and an abdomen effort sensor.

FIG. 20 graphs several distinct effort signals from different sensors on a common time scale in relation to various sleep disordered breathing events. The sleep disordered breathing events are represented in a flow signal 2002 and include obstructive apnea OA, central apnea CA and central hypopnea CH and obstructive hypopnea OH. Beneath the flow signal 2002 is a graph of a thoracic effort signal 2018 from a thoracic effort sensor that detects effort from a thoracic area of a patient's body. The next signal down is an abdominal effort signal 2020 from an abdominal effort sensor that detects effort from an abdominal area of a patient's body. The last two signals are head strain effort signals 2004-L, 2004-R from left and right side head strain sensors respectively of the present technology that detect effort from a head area of a patient's body.

Again, it is the combination of reduced flow and the presence of respiratory effort that indicates the presence of obstructive apnea or hypopnea. In contrast, a combination of a reduced flow with the absence of a respiratory effort indicates a central apnea or hypopnea. One or more of the signals displayed in FIG. 20 may be implemented in some embodiments of the present technology. As discussed in the above text, various forms of processing, such as filtering or summation, can also be applied to the raw signals. For example, the filtering processes previously mentioned with respect to FIGS. 14-19 may be applied to the signals of any of these sensors such as for distinguishing types of sleep disordered breathing events.

While the technology has been described in connection with what are presently considered to be the most practical and preferred embodiments, it is to be understood that the proposed technology is not to be limited to the disclosed examples, but on the contrary, is intended to cover various modifications and equivalent arrangements included within the spirit and scope of the entire specification. Also, the various embodiments described above may be implemented in conjunction with other embodiments, e.g., aspects of one embodiment may be combined with aspects of another embodiment to realize yet other embodiments. Further, one or more independent features or component of any given embodiment may constitute an additional embodiment.

For example, while an integrated device is contemplated by the present technology, the methodology of the components of the devices may be shared across multiple components of a system. For example, a monitoring device may simply measure the strain signals of the patient and transfer the data representing those signals to another processing system. The second processing system may in turn analyze the data to determine the respiratory effort or related data and metrics therefrom such as the sleep disordered breathing event. The second processing system may then evaluate and generate warning messages as described herein, such as by sending one or more of the described messages, in electronic form for example, back to the patient monitoring device for display on the device to warn the patient.

In addition, while the described technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

Accordingly, an example of the above technology may involve a method for discriminating between effort and no effort apneas, including, determining a threshold headgear tension, measuring a first headgear tension at a certain time, comparing the first headgear tension to the threshold headgear tension, and determining if an effort apnea has occurred if the first headgear tension is greater than the threshold headgear tension.

Also, whilst the embodiments of FIGS. 3 to 10 show primarily strain sensors arranged to measure strain at various points of the face, it should be noted that such sensors can similarly be positioned to measure strain at various points of the neck, the forehead or other parts of the head.

Other variations can be made without departing with the spirit and scope of the technology.

The invention claimed is:

1. A method for detecting respiratory related effort comprising:
using a sensor to generate a strain signal, the strain signal including one or both of a mouth strain signal and a jaw strain signal, the sensor being configured with a respiratory mask or headgear of a respiratory treatment apparatus to sense mask force or headgear tension, the headgear tension concerning change in tension of a strap of the headgear, wherein the sensor is configured to generate the strain signal in response to movement of one or both of a user's mouth and jaw;
receiving the strain signal and a flow signal from a flow sensor in a processor, and
detecting breathing related events in the processor with the flow signal and strain signal, the detecting comprising analyzing the strain signal in the processor to detect respiratory related effort,
wherein the analyzing comprises a comparison of the strain signal and a threshold value;
and automatically controlling a change to a respiratory treatment variable in a controller of the respiratory treatment apparatus, based on the analyzing of the strain signal and the flow signal.

2. The method of claim 1 wherein the threshold is derived from a prior mouth strain signal or jaw strain signal measured with the sensor.

3. The method of claim 1 wherein the method further comprises indicating, with the processor, a type of detected apnea or hypopnea based on the analyzing of the strain signal, wherein the type of detected apnea or hypopnea is identified as one of central, obstructive or mixed, depending on a presence of respiratory effort.

4. The method of claim 1 further comprising identifying, with the processor, a respiratory related arousal event based on the comparison.

5. The method of claim 1 wherein the sensor comprises a strain gauge, a piezoresistor, a tensometer or a spring gauge.

6. The method of claim 5 wherein the sensor is a component of headgear.

7. The method of claim 6, wherein the sensor is configured to detect changes in tension of one or more straps of the headgear.

8. The method of claim 6 wherein the sensor is configured to detect changes in head or face contact compression with a portion of the headgear.

9. The method of claim 5 wherein the sensor is a component of headgear for a patient interface for a respiratory treatment apparatus, the patient interface comprising a respiratory mask and a breathable gas conduit.

10. The method of claim 5 wherein the sensor is a component of a patient interface for a respiratory treatment apparatus, the patient interface comprising a respiratory mask and a breathable gas conduit.

11. The method of claim 1 wherein the respiratory treatment variable comprises pressure.

12. The method of claim 1, wherein the step of analyzing the strain signal with a processor comprises:
generating a first and a second filtered strain signals based on the strain signal;
making a comparison based on the first and the second filtered strain signals; and
generating an indicator of a presence or absence of significant respiratory effort based on the comparison.

13. The method of claim 12, wherein the comparison includes comparing the second filtered strain signal with a proportion of the first filtered strain signal.

14. The method of claim 13, wherein the first filtered strain signal comprises a first average strain signal determined over a first period of time, and the second filtered strain signal comprises a second average strain signal determined over a second period of time, wherein the first period of time is longer than the second period of time.

15. The method of claim 12, wherein an obtained indication of strain of one or both of the user's mouth and jaw is used to classify an apnea or a hypopnea as an obstructive event.

16. The method of claim 12, wherein an obtained indication of an absence of strain of one or both of the user's mouth and jaw is used to classify an apnea or a hypopnea as a central event.

17. The method of claim 12, wherein the first and second filtered strain signals are derived from a plurality of strain signals.

18. The method of claim 16, wherein each of the first and the second filtered strain signals is derived from a combined strain signal representing a sum of multiple strain signals.

19. A device for detecting a respiratory related effort comprising:
- one or more sensors configured with a respiratory mask or headgear to generate a strain signal, the strain signal including one or both of a mouth strain signal and a jaw strain signal, the one or more sensors configured to sense mask force or headgear tension, the headgear tension concerning change in tension of a strap of the headgear, wherein the sensor is configured to generate the strain signal in response to movement of one or both of a user's mouth and jaw;
- a flow sensor configured to generate a flow signal, and
- a processor, coupled with the one or more sensors and the flow sensor, the processor configured to control detection of breathing events with the flow signal and the strain signal, the detection comprising detection of respiratory related effort by analysis of the strain signal, wherein the analysis comprises a comparison of the strain signal and a threshold value; and wherein the processor is configured to automatically control a change to a respiratory treatment variable setting based on the analysis of the strain signal and the flow signal.

20. The device of claim 19 wherein the threshold is derived from a prior mouth strain signal or jaw strain signal measured with the strain sensor.

21. The device of claim 19 wherein the processor is configured to identify a type of detected apnea or hypopnea, based on the analyzing of the strain signal, as one of central, obstructive or mixed, depending on the presence of respiratory effort.

22. The device of claim 19 wherein the processor is configured to identify a respiratory related arousal event based on the comparison.

23. The device of claim 19, wherein the strain sensor comprises a strain gauge, a piezoresistor, a tensometer or a spring gauge.

24. The device of claim 23 wherein the sensor is a component of headgear.

25. The device of claim 24, wherein the strain sensor is configured to detect changes in tension of one or more straps of the headgear.

26. The device of claim 24 wherein the strain sensor is configured to detect changes in head or face contact compression with a portion of the headgear.

27. The device of claim 23 wherein the strain sensor comprises a component of headgear for a patient interface for a respiratory treatment apparatus, the patient interface comprising a breathable gas conduit.

28. The device of claim 23 wherein the strain sensor comprises a component of a patient interface for a respiratory treatment apparatus, the patient interface comprising a respiratory mask and a breathable gas conduit.

29. The device of claim 19 wherein the respiratory treatment variable comprises pressure.

30. The device of claim 19, wherein the processor is configured for analyzing the strain signal by way of:
- generating a first and a second filtered strain signals based on the generated strain signal;
- making a comparison based on the first and the second filtered strain signals, and
- generating an indicator of a presence or absence of significant respiratory effort based on the comparison.

31. The device of claim 30, wherein the comparison includes comparing the second filtered strain signal with a proportion of the first filtered strain signal.

32. The device of claim 30 wherein the first filtered strain signal comprises a first average strain signal over a first period of time and the second filtered strain signal comprises a second average strain signal determined over a second period of time, wherein the first period of time is longer than the second period of time.

33. The device of claim 30, wherein an obtained indication of a strain of one or both of the user's mouth and jaw is used to classify an apnea or a hypopnea as an obstructive event.

34. The device of claim 30, wherein an obtained indication of an absence of a strain of one or both of the user's mouth and jaw is used to classify an apnea or a hypopnea as a central event.

35. The device of claim 30, wherein the first and second filtered strain signals are derived from a plurality of strain signals.

36. The device of claim 35, wherein each of the first and the second filtered strain signals is derived from a combined strain signal representing a sum of multiple strain signals.

37. A respiratory treatment apparatus comprising:
- a patient interface including a respiratory mask and headgear, the patient interface comprising one or more sensors configured with the patient interface or the headgear to generate a strain signal, the strain signal including one or both of a mouth strain signal and a jaw strain signal, the one or more sensors configured to sense mask force or headgear tension, the headgear tension concerning change in tension of a strap of the headgear, wherein the sensor is configured to generate the strain signal in response to movement of one or both of a user's mouth and jaw;
- a flow generator adapted to be coupled to the patient interface and to generate a flow a breathable gas through the patient interface;
- a flow sensor to generate a flow signal; and
- a processor, coupled with the flow generator and adapted to couple with the one or more sensors and the flow sensor, the processor configured to control the flow generator, and to control a detection of breathing events with the flow signal and the strain signal, the detection comprising detection of respiratory related effort by analysis of the strain signal,
- wherein the analysis comprises a comparison of the strain signal and a threshold value; and wherein the processor is configured to automatically control a change to a respiratory treatment variable setting of the flow generator based on the analysis of the strain signal and the flow signal.

38. The apparatus of claim 37 wherein the threshold is derived from a prior mouth strain signal or jaw strain signal measured with the one or more sensors.

39. The apparatus of claim 37 wherein the processor is configured to identify a type of a detected apnea or hypopnea, based on the analyzing of the strain signal, as one of central, obstructive or mixed, based on the presence of respiratory effort.

40. The apparatus of claim 37 wherein the processor is also configured to identify a respiratory related arousal event based on the comparison.

41. The apparatus of claim 37 wherein at least one of the one or more sensors comprises a strain gauge, a piezoresistor, a tensometer or a spring gauge.

42. The apparatus of claim 41 wherein at least one of the one or more sensors comprises a component of headgear.

43. The apparatus of claim 42, wherein the one or more sensors are configured to detect changes in tension of one or more straps of the headgear.

44. The apparatus of claim 42 wherein the one or more sensor are configured to detect changes in head or face contact compression with a portion of the headgear.

45. The apparatus of claim 41 wherein at least one of the one or more sensors is a component of a respiratory mask.

46. The apparatus of claim 37 wherein the respiratory treatment variable comprises pressure.

47. The apparatus of claim 37, wherein the processor is configured for analyzing the strain signal by way of:
generating a first and a second filtered strain signals based on the generated strain signal;
making a comparison based on the first and the second filtered strain signals; and
generating an indicator of a presence or absence of significant respiratory effort based on the comparison.

48. A patient interface device for a respiratory treatment apparatus, the patient interface device comprising:
a respiratory mask and headgear supporting the mask;
one or more sensors configured with the respiratory mask or the headgear to generate a strain signal, the strain signal including one or both of a mouth strain signal and a jaw strain signal, the one or more sensors configured to sense mask force or headgear tension, the headgear tension concerning change in tension of a strap of the headgear, wherein one or more sensors is configured to generate the strain signal in response to movement of one or both of a user's mouth and jaw, the one or more sensors being adapted for coupling with a signal interface of a processor of a respiratory treatment apparatus for detection of breathing events with a flow signal of a flow sensor and the strain signal, the detection comprising detection of respiratory related effort by analysis of the strain signal and a threshold value,
wherein a change to a respiratory treatment variable setting is based on the analysis of the strain signal and the flow signal, and wherein the patient interface device is configured to conduct a flow of breathable gas from a flow generator of the respiratory treatment apparatus.

49. The device of claim 48 wherein at least one of the one or more sensors comprises a strain gauge, a piezoresistor, a tensometer or a spring gauge.

50. The device of claim 49 wherein at least one of the one or more sensors comprises a component of the headgear.

51. The device of claim 50, wherein at least one of the one or more sensors is configured to detect changes in tension of the headgear.

52. The device of claim 49 wherein at least one of the one or more sensors is configured to detect changes in head, neck or face contact compression with a portion of the patient interface.

53. The device of claim 48 wherein at least one of the one or more sensors is a component of the mask.

54. The method of claim 1 wherein the sensor is configured with a respiratory mask of a respiratory treatment apparatus to sense mask force.

55. The method of claim 1 wherein the sensor is configured with headgear of a respiratory treatment apparatus to sense headgear tension.

56. The device of claim 19 wherein the one or more sensors are configured with a respiratory mask of a respiratory treatment apparatus to sense mask force.

57. The device of claim 19 wherein the one or more sensors are configured with headgear of a respiratory treatment apparatus to sense headgear tension.

58. The respiratory treatment apparatus of claim 37 wherein the one or more sensors are configured with a respiratory mask of a respiratory treatment apparatus to sense mask force.

59. The respiratory treatment apparatus of claim 37 wherein the one or more sensors are configured with headgear of a respiratory treatment apparatus to sense headgear tension.

60. The patient interface device of claim 48 wherein the one or more sensors are configured with headgear of a respiratory treatment apparatus to sense headgear tension.

61. The patient interface device of claim 48 wherein the one or more sensors are configured with a respiratory mask of a respiratory treatment apparatus to sense mask force.

62. The method of claim 1, further comprising determining, with the processor, a type of detected apnea or hypopnea, based on the analyzing of the strain signal.

* * * * *